(12) United States Patent
Fleisher et al.

(10) Patent No.: US 10,067,050 B2
(45) Date of Patent: Sep. 4, 2018

(54) LINEAR ABSORPTION SPECTROMETER TO OPTICALLY DETERMINE AN ABSOLUTE MOLE FRACTION OF RADIOCARBON IN A SAMPLE

(71) Applicant: The United States of America, as Represented by the Secretary of Commerce, Washington, DC (US)

(72) Inventors: Adam J. Fleisher, Gaithersburg, MD (US); David A. Long, Bethesda, MD (US); Joseph T. Hodges, Washington Grove, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/596,243

(22) Filed: May 16, 2017

(65) Prior Publication Data

US 2018/0156718 A1     Jun. 7, 2018

Related U.S. Application Data

(60) Provisional application No. 62/430,129, filed on Dec. 5, 2016.

(51) Int. Cl.
*G01N 21/00* (2006.01)
*G01N 21/27* (2006.01)
(Continued)

(52) U.S. Cl.
CPC ............ *G01N 21/27* (2013.01); *G01J 3/0208* (2013.01); *G01J 3/0286* (2013.01);
(Continued)

(58) Field of Classification Search
CPC ...... G01N 21/27; G01N 21/255; G01N 21/84; G01N 33/0036; G01N 33/497;
(Continued)

(56) References Cited

U.S. PATENT DOCUMENTS 5,528,040 A    6/1996  Lehmann
5,621,209 A    4/1997  Purser
(Continued)

OTHER PUBLICATIONS

A. D. McCartt, "Quantifying carbon-14 for biology using cavity ring-down spectroscopy", Analytical Chemistry, 2016, 8714-8719, 88.
(Continued)

*Primary Examiner* — Isiaka Akanbi
(74) *Attorney, Agent, or Firm* — Office of Chief Counsel for National Institute of Standards and Technology

(57) ABSTRACT

A linear absorption spectrometer includes: a laser light source that provides mid-infrared laser light; a high finesse optical resonator that includes: a sample cell operating at a temperature from 220 K to 300 K during linear absorption of mid-infrared laser light by radiocarbon and including: a linear absorption optical path length greater than a kilometer; a first zero-pressure difference mirror mount on which a first supermirror is disposed; a second zero-pressure difference mirror mount on which a second supermirror is disposed; an optical switch interposed between the laser light source and the high finesse optical resonator that modulates and communicates mid-infrared laser light to the high finesse optical resonator; a photoreceiver that receives cavity ring down light and includes a noise equivalent power that is less than a shot noise limit of cavity ring down light.

18 Claims, 25 Drawing Sheets

(51) Int. Cl.
*G01N 21/84* (2006.01)
*G01N 21/25* (2006.01)
*G01N 33/00* (2006.01)
*G01N 33/497* (2006.01)
*G01J 3/02* (2006.01)

(52) U.S. Cl.
CPC ............ *G01N 21/255* (2013.01); *G01N 21/84* (2013.01); *G01N 33/0036* (2013.01); *G01N 33/497* (2013.01); *G01N 2033/0093* (2013.01); *G01N 2033/4975* (2013.01)

(58) Field of Classification Search
CPC .... G01N 2033/0093; G01N 2033/4975; G01J 3/0208; G01J 3/0286
USPC .......................................... 356/436–437, 440
See application file for complete search history.

(56) References Cited

U.S. PATENT DOCUMENTS

| | | | | |
|---|---|---|---|---|
| 5,903,358 | A * | 5/1999 | Zare | G01J 3/10 250/343 |
| 6,466,322 | B1 * | 10/2002 | Paldus | G01N 21/39 356/437 |
| 6,865,198 | B2 | 3/2005 | Taubman | |
| 7,154,595 | B2 | 12/2006 | Paldus et al. | |
| 8,063,373 | B2 | 11/2011 | Miller | |
| 8,154,727 | B2 | 4/2012 | Dreyer et al. | |
| 9,329,123 | B2 | 5/2016 | Harb | |
| 2009/0185175 | A1 * | 7/2009 | Cole | G01J 1/44 356/213 |
| 2009/0213463 | A1 * | 8/2009 | Cole | G01J 3/02 359/584 |
| 2014/0347662 | A1 * | 11/2014 | Hodges | G02B 26/001 356/326 |
| 2016/0054180 | A1 | 2/2016 | Guisfredi et al. | |

OTHER PUBLICATIONS

I. Galli, et al., "Spectroscopic detection of radiocarbon dioxide at parts-per-quadrillion sensitivity", Optica 3, 2016, 385-388, 3.

G. Guisfredi, et al.,"Theory of saturated-absorption cavity ring-down: radiocarbon dioxide detection, a case study", Journal of the Optical Society of America B, 2015, 2223-2237, 32.

G. Genoud, et al., "Radiocarbon dioxide detection based on cavity ring-down spectroscopy and a quantum cascade laser," Optics Letters, 2015, 1342-1345, 40.

A. D. McCartt, et al.,"Measurements of carbon-14 with cavity ring-down spectroscopy", Nuclear Instruments and Methods in Physics Research Section B: Beam Interactions with Materials and Atoms, 2015 , 277-280, 361.

P. Cancio, et al., "Saturated-absorption cavity ring-down (SCAR) for high-sensitivity and high-resolution molecular spectroscopy in the mid IR", Cavity-Enhanced Spectroscopy and Sensing, G. Gagliardi and H.-P. Loock, eds. (Springer-Verlag, Berlin, 2014), 143-162.

A. D. McCartt, "Development of a low-temperature cavity ring-down spectrometer for the detection of carbon-14", Ph.D. thesis, Stanford University, Jul. 2014.

I. Galli, et al., "Optical detection of radiocarbon dioxide: first results and AMS intercomparison", Radiocarbon, 2013, 213-223, 55.

I. Galli, et al., "The V3 band of 14-C 16-O2 molecule measured by optical-frequency-comb-assisted cavity ring-down spectroscopy", Molecular Physics, 2011, 2267-2272, 109.

I. Galli, et al., "Molecular gas sensing below parts per trillion: radiocarbon-dioxide optical detection", Physical Review Letters, 2011, 270802, 107 ; Erratum Physical Review Letters, 2012, 179902, 108.

* cited by examiner (A)

(B)

US 10,067,050 B2

LINEAR ABSORPTION SPECTROMETER TO OPTICALLY DETERMINE AN ABSOLUTE MOLE FRACTION OF RADIOCARBON IN A SAMPLE

CROSS REFERENCE TO RELATED APPLICATIONS

This application claims the benefit of U.S. Provisional Patent Application Ser. Nos. 62/430,129, filed Dec. 5, 2016, the disclosure of which is incorporated herein by reference in its entirety.

STATEMENT REGARDING FEDERALLY SPONSORED RESEARCH

This invention was made with United States Government support from the National Institute of Standards and Technology, an agency of the United States Department of Commerce. The Government has certain rights in the invention.

BRIEF DESCRIPTION

Disclosed is a linear absorption spectrometer to optically determine an absolute mole fraction of radiocarbon in a sample, the linear absorption spectrometer comprising: a laser light source that provides mid-infrared laser light for linear absorption by the radiocarbon in the sample; a high finesse optical resonator that is actively stabilized in a resonance frequency and comprising: a first supermirror comprising a first radius of curvature that provides cavity ring down reflection and that receives the mid-infrared laser light; a second supermirror comprising a second radius of curvature that provides cavity ring down reflection, the second supermirror in combination with the first supermirror comprises a relative difference of refractive index $\Delta n/n$ from $1\times 10^{-8}$ to $6\times 10^{-6}$, such that the second supermirror transmits cavity ring down light from communicating the mid-infrared laser light through the sample in a sample cell; the sample cell interposed between the first supermirror and the second supermirror to contain the sample, the sample cell operating at a temperature from 180 K to 300 K during linear absorption of the mid-infrared laser light by the radiocarbon and comprising: a linear absorption optical path length that is greater than a kilometer (km); a first zero-pressure difference mirror mount on which the first supermirror is disposed and mechanically coupled to the sample cell; a second zero-pressure difference mirror mount on which the second supermirror is disposed and mechanically coupled to the sample cell; an optical switch interposed between the laser light source and the high finesse optical resonator such that the optical switch receives the mid-infrared laser light from the laser light source, modulates the mid-infrared laser light, and communicates modulated mid-infrared laser light to the first supermirror of the high finesse optical resonator; a photoreceiver in optical communication with the high finesse optical resonator and that receives the cavity ring down light from the second supermirror, the photoreceiver comprising a noise equivalent power that is less than a shot noise limit of the cavity ring down light, the linear absorption spectrometer providing the absolute mole fraction of the radiocarbon in the sample for the absolute mole fraction being from 1 part-per-quadrillion to 2.5 parts-per-trillion of radiocarbon in the sample.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a linear absorption spectrometer herein provides optical detection of radiocarbon ($^{14}$C) in a sample (e.g., gaseous carbon dioxide (CO$_2$) that includes a combination of carbon isotopes) with a sensitivity below modern picomole per mole levels (e.g., $^{14}$C/$^{12}$C<10$^{-12}$). The linear absorption spectrometer includes a high-finesse optical resonator with a sample cell that includes cryogenic cooling, refrigerant cooling, and is vacuum compatible. As a result, the linear absorption spectrometer provides determination of the amount of the radiocarbon in a stable, low temperature gas environment during optical analysis and reduces spectral interferences. Optical detection of the radiocarbon in the sample is via linear absorption, wherein nonlinear molecular absorption does not compromise a measured cavity decay time of signal from the sample cell. Also, it is contemplated that a laser diode in an absence of high-bandwidth phase locking or laser stabilization is used in some embodiments of the linear absorption spectrometer.

Conventional radiocarbon analysis is performed at accelerator mass spectrometry (AMS) facilities that are expensive to construct and whose operation involves a team of technicians and scientists. The linear absorption spectrometer significantly reduces cost and provides automation of spectral analysis to reduce the time for radiocarbon analysis. The elimination of current financial and analysis time costs provide availability for radiocarbon analysis across geoscience, biology, atmospheric chemistry, archeology, and the like.

Figure 1:
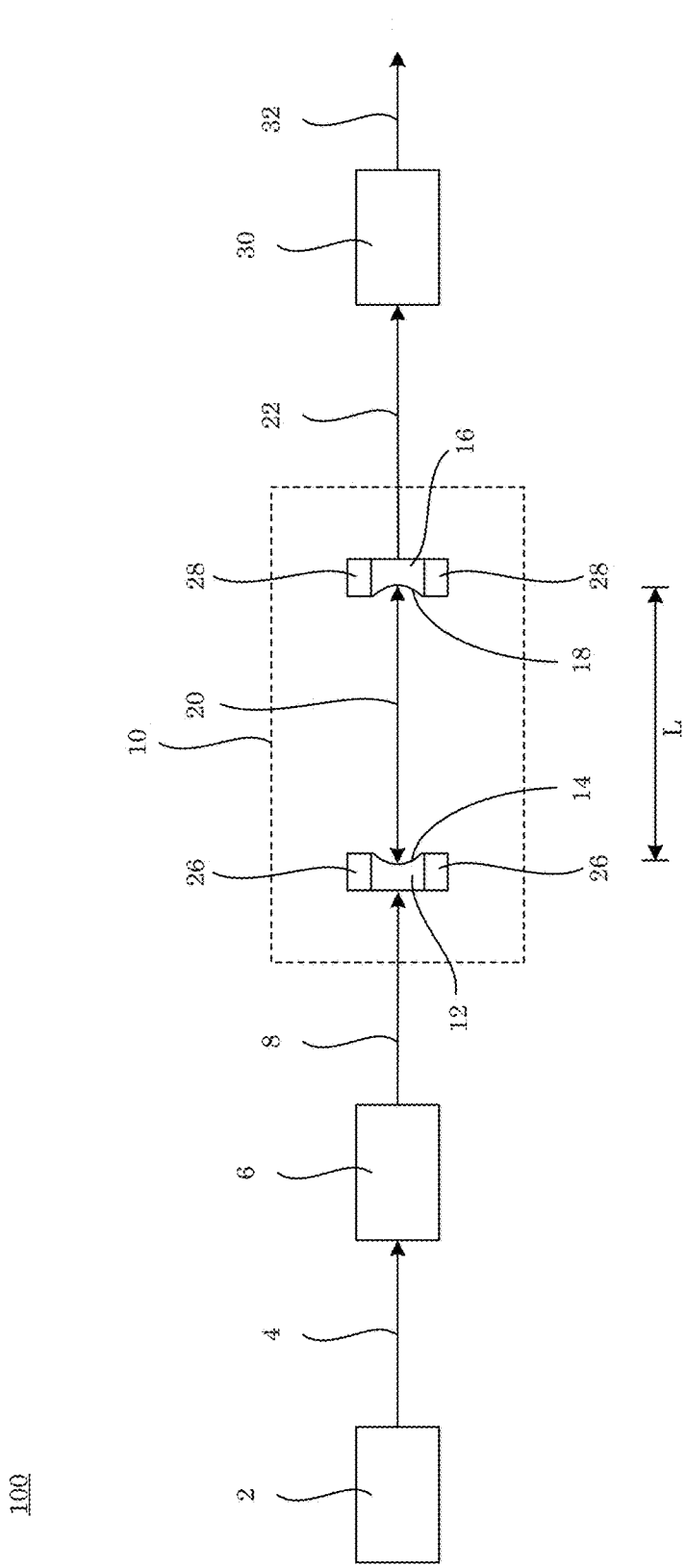
FIG. 1 shows an linear absorption spectrometer.

In an embodiment, with reference to FIG. 1, linear absorption spectrometer 100 optically determines an absolute mole fraction and number density of radiocarbon in a sample and includes laser light source 2 that provides mid-infrared laser light 4 for linear absorption by the radiocarbon in the sample; high finesse optical resonator 10 that is actively stabilized in a resonance frequency. High finesse optical resonator 10 includes first supermirror 12 including a first radius of curvature at reflection surface 14 that provides cavity ring down reflection and that receives mid-infrared laser light 4; second supermirror 16 including a second radius of curvature at reflection surface 18 that provides cavity ring down reflection, second supermirror 16 in combination with first supermirror 12 includes a relative difference of refractive index $\Delta n/n$ from 1×10$^{-8}$ to 6×10$^{-6}$, such that second supermirror 16 transmits cavity ring down light 22 from communicating mid-infrared laser light 20 through the sample in sample cell 24; sample cell 24 interposed between first supermirror 12 and second supermirror 16 to contain the sample, sample cell 24 operating at a temperature from 180 K to 300 K during linear absorption of mid-infrared laser light 20 by the radiocarbon and including a linear absorption optical path length that is greater than a kilometer (km); first zero-pressure difference mirror mount 26 on which first supermirror 12 is disposed and mechanically coupled to sample cell 24; second zero-pressure difference mirror mount 28 on which second supermirror 16 is disposed and mechanically coupled to sample cell 24; optical switch 6 interposed between laser light source 2 and high finesse optical resonator 10 such that optical switch 6 receives mid-infrared laser light 4 from laser light source 2, modulates mid-infrared laser light 4, and communicates modulated mid-infrared laser light 8 to first supermirror 12 of high finesse optical resonator 10; photoreceiver 30 in optical communication with high finesse optical resonator 10 and that receives cavity ring down light 22 from second supermirror 16, photoreceiver 30 including a noise equivalent power that is less than a shot noise limit of cavity ring down light 22, linear absorption spectrometer 100 providing the absolute mole fraction and number density of the radiocarbon in the sample for the absolute mole fraction being from 1 part-per-quadrillion to 2.5 parts-per-trillion of radiocarbon in the sample. Here, the sample that includes the radiocarbon disposed in interior 34 of sample cell 24 such that the sample is subjected to mid-infrared laser light 20 in a plurality of reflections of mid-infrared laser light 20 from reflection surface 14 of first supermirror 12 and reflection surface 18 of second supermirror 16.

Figure 2:
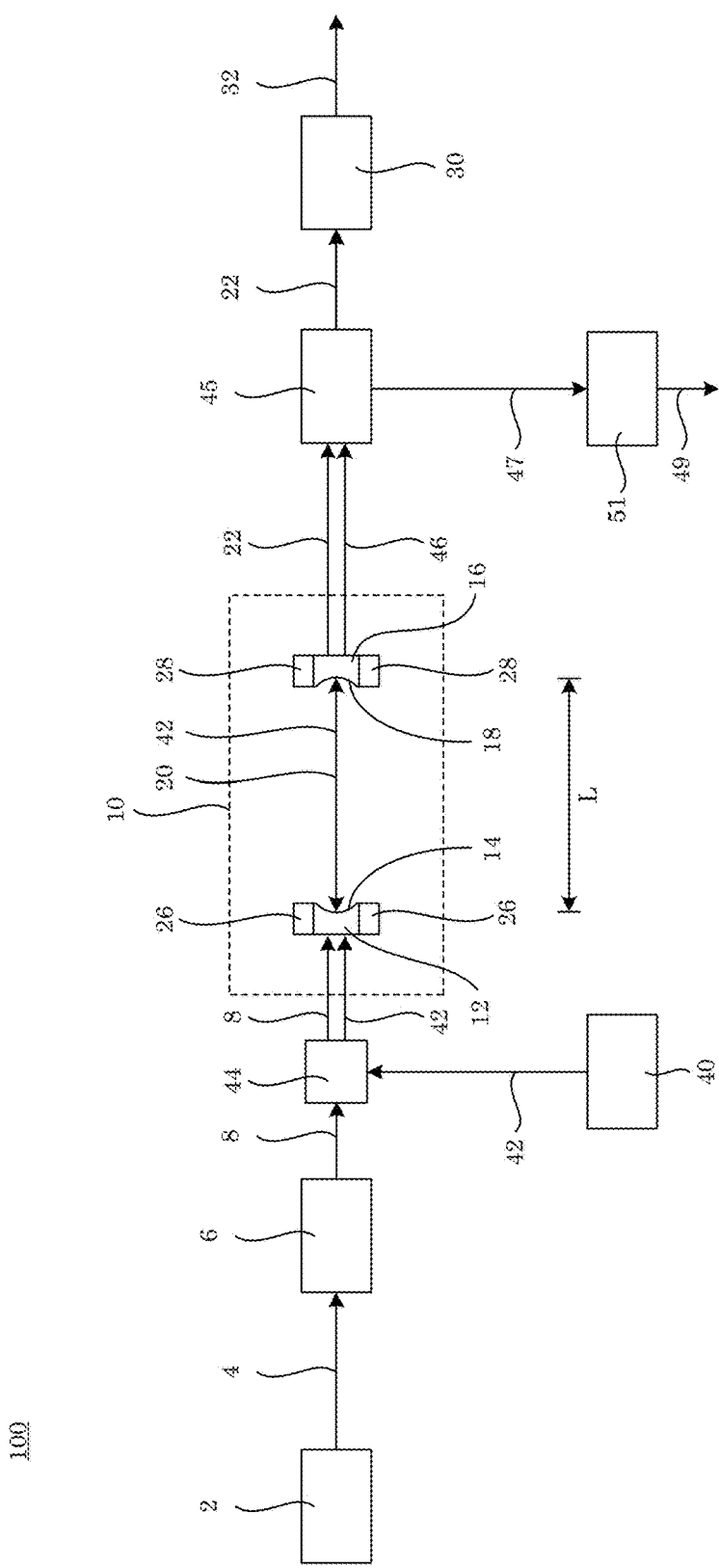
FIG. 2 shows an linear absorption spectrometer.

In an embodiment, with reference to FIG. 2, linear absorption spectrometer 100 includes reference laser 40 that provides reference laser light 42 and optical combiner 44 that receives reference laser light 42 from reference laser 40 and modulated mid-infrared laser light 8 from optical switch 6. Optical mirror 44 combines mid-infrared laser light 8 and reference laser light 42 and communicates mid-infrared laser light 8 and reference laser light 42 to high finesse optical resonator 10, wherein first supermirror 12 receives mid-infrared laser light 8 and reference laser light 42. Second supermirror 16 transmits cavity ring down light 22 and reference light 46 to beam splitter 45. Beam splitter 45 splits cavity ring down light 22 and reference laser light 46, wherein cavity ring down light 22 is communicated to and received by photo receiver 30 that produces absorption signal 32 in response to receipt of cavity ring down light 22 from beam splitter 45. Further, reference laser light 46 is received by photo receiver 51 from beam splitter 45 and produces reference laser signal 49 in response to receipt of reference laser light 46. In this manner, linear absorption spectrometer 100 provides reference laser signal 49 and absorption signal 32 so that absorption signal 32 is proportional to the absorption spectrum of sample radiocarbon and reference signal 49 is a discriminant signal quantifying change in the cavity resonance frequency with fractional stability greater than 1 in $10^8$.

Figure 3:
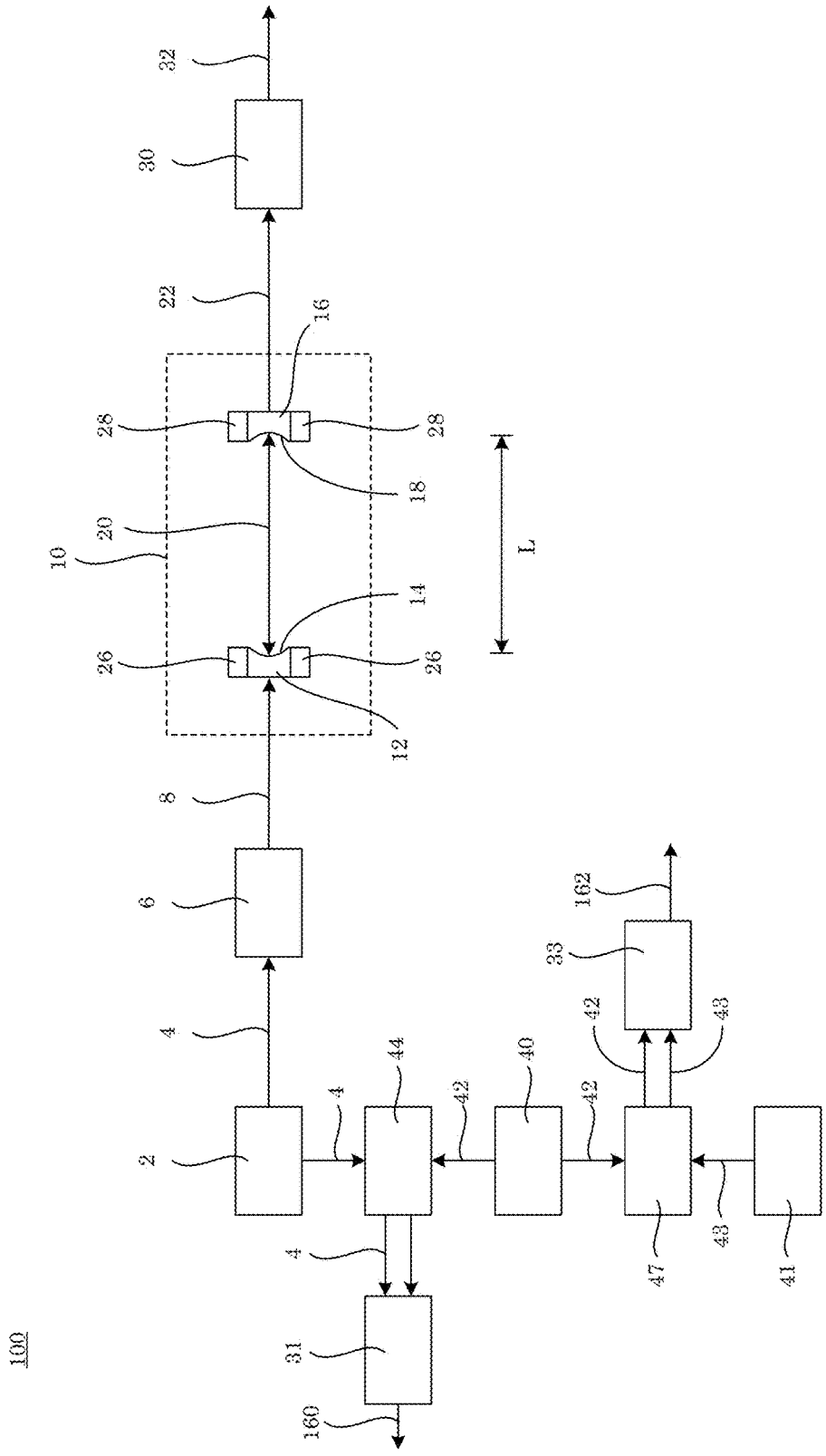
FIG. 3 shows an linear absorption spectrometer.

In an embodiment, with reference to FIG. 3, linear absorption spectrometer 100 includes reference laser 40 that produces reference laser light 42 that is received by optical combiner 44. Optical combiner 44 also receives mid-infrared laser light 4 from laser light source 2, combines light (4, 42), and communicates light (4, 42) to photo receiver 31 that produces first reference signal 160 in response to receipt of light (4, 42). Here, first reference signal 160 is a beat signal between mid-infrared laser light 4 and reference laser light 42. Additionally, reference light 42 from reference laser 40 is communicated to beam combiner 47 that receives comb laser light 43 from mid-infrared frequency comb 41. Beam combiner 47 combines and communicates reference laser light 42 and comb laser light 43 to photo receiver 33. Photo receiver 33 produces second reference signal 162 in response to receipt of reference laser light 42 and comb laser light 43. Here, second reference signal 162 is an electrical beat signal between reference laser light 42 and comb laser light 43. First reference signal 160 and second reference signal 162 are used to establish frequency linkage between mid-infrared laser light 2 optical frequency comb 41.

Figure 4:
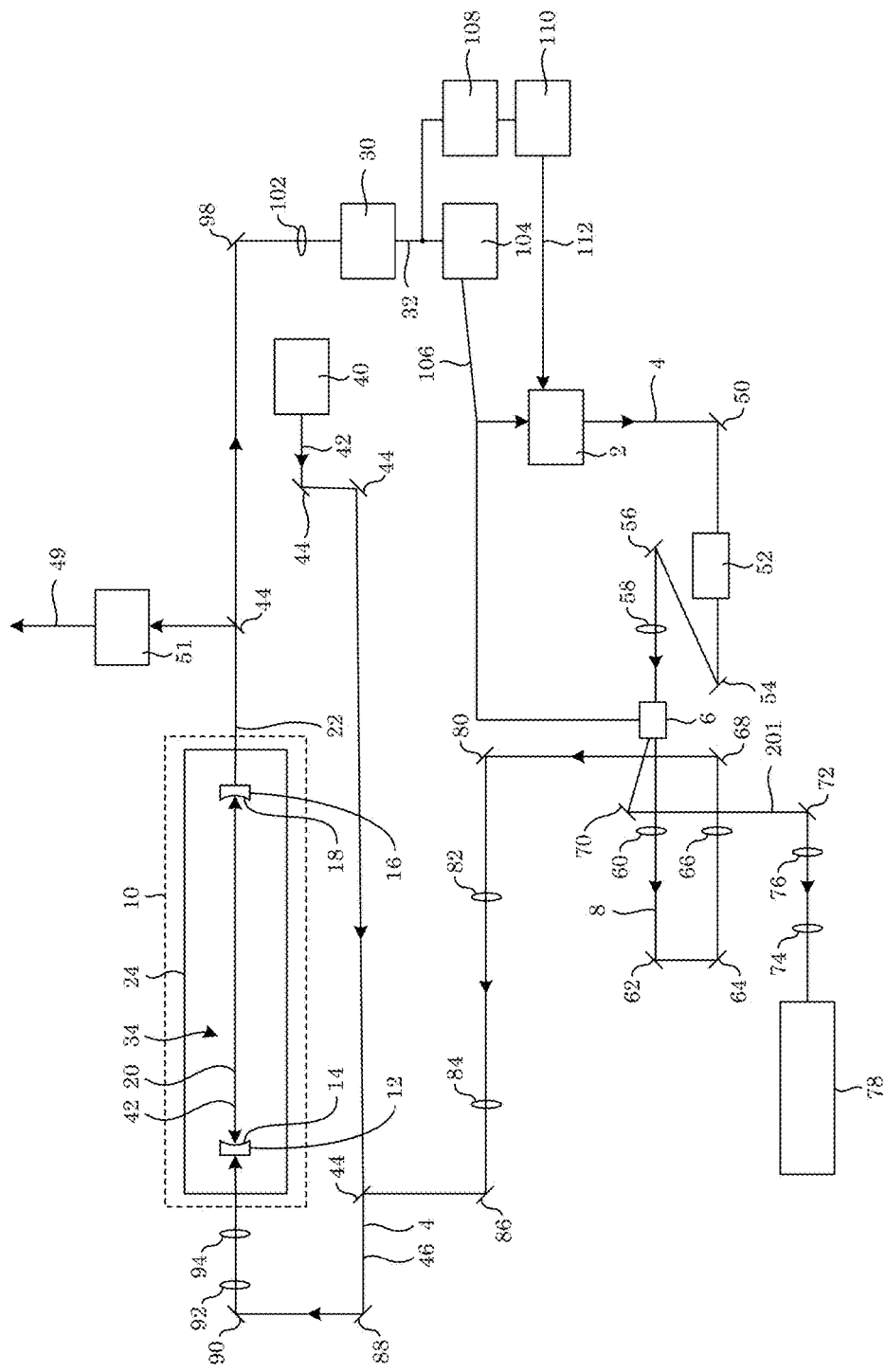
FIG. 4 shows an linear absorption spectrometer.

According to an embodiment, with reference to FIG. 4, linear absorption spectrometer 100 includes quantum cascade laser 2 that produces and communicates mid-infrared laser light 4 as reflected from mirror 50 to optical isolator 52. Mid-infrared laser light 4 reflects from mirrors 54 and 56 and communicates through lens 58. Optical switch 6 (e.g., an acousto-optic modulator) receives and modulates mid-infrared laser light 4. Wavemeter 78 receives mid-infrared laser light 4 from acousto-optic modulator 6 via mirrors (70, 72) and lenses (74, 76). Moreover, mid-infrared laser light 4 is communicated from acousto-optic modulator 6 to optical resonator 10 via mirrors (62, 64, 68, 80, 86, 44, 88, 90), lenses (60, 66, 82, 84), half-wave plate 92 and polarization analyzer 94. Linear absorption spectrometer 100 also includes reference laser 40 (e.g., a helium neon stabilized frequency reference laser) that communicates reference laser light 42 to high finesse optical resonator 10 via mirrors (44, 88, 90). Cavity ring down light 22 is communicated from second supermirror 16 through polarization analyzer 96, lenses 102 and mirror 98 to photo receiver 30 that is produces absorption signal 32 therefrom. Absorption signal 32 is communicated to delay generator 104 and digitizer 108. Delay generator 100 for produces and communicates delay signal 106 to quantum cascade laser 2 and acousto-optic modulator 6. Digitizer 108 produces a digitized signal of analog absorption signal 32 from photo receiver 30 and communicates the digitized signal to processor 110 (e.g., a computer or the like).

Figure 5:
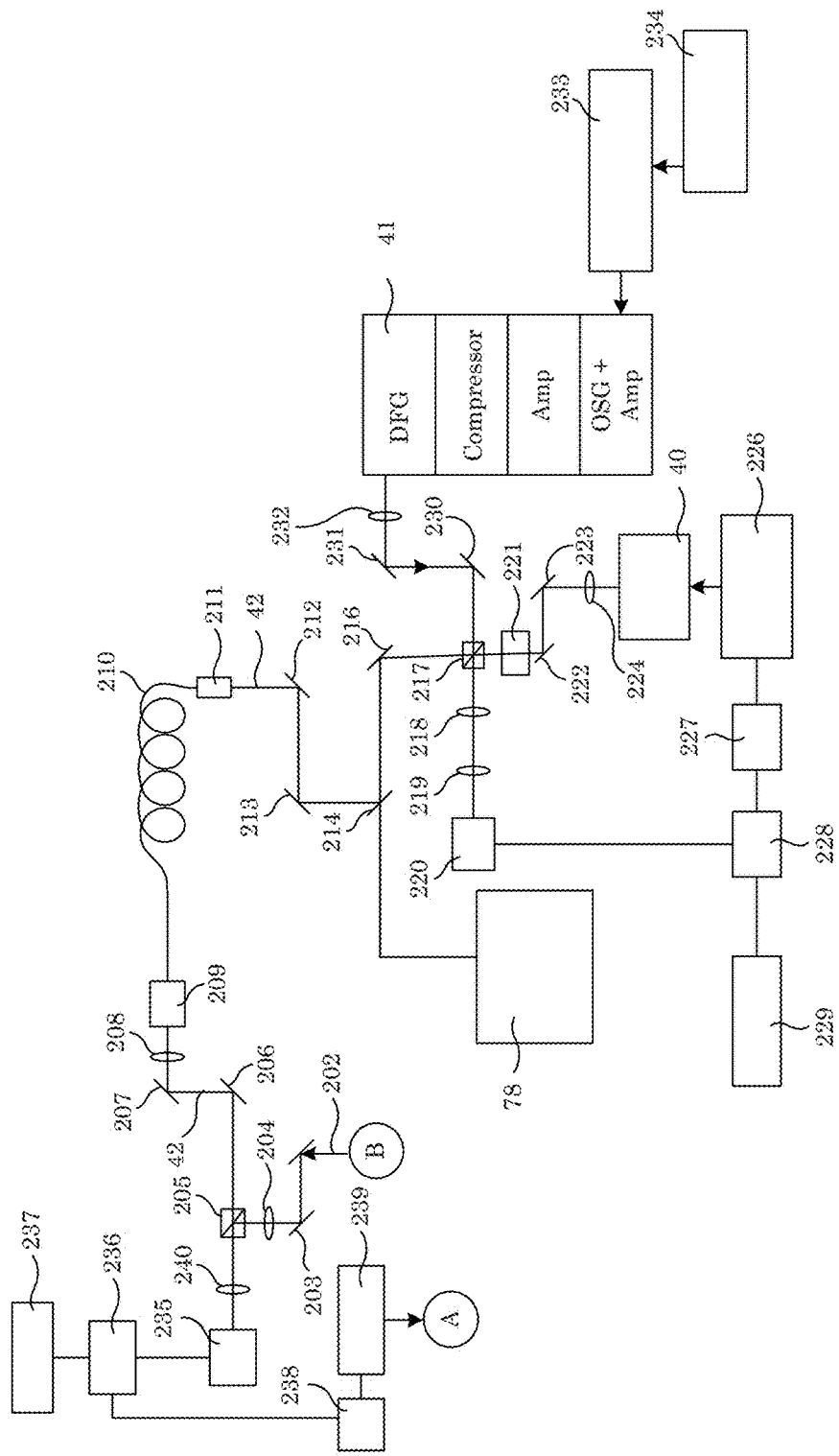
FIG. 5 shows an linear absorption spectrometer.

In an embodiment, with reference to FIG. 5, linear absorption spectrometer 100 includes optical frequency comb 41 and reference laser 40. Here, radiofrequency clock 234 (e.g., optical clock, rubidium clock, cesium clock, global positioning system time base, quartz oscillator, and the like) provides a frequency signal to comb controller 233 that provides control signal to an oscillator in amplifier of optical frequency comb 41. Laser light from frequency comb 41 is combined on photoreceiver 220 with laser light from reference laser 40. Reference laser 40 is a semiconductor laser, specifically a quantum cascade laser, or the like. Frequency comb 41 is transmitted to photoreceiver 220 by mirrors (231, 230), through half-wave plate 232, polarization beam splitter 217, polarization analyzer 218, and lens 219. Reference laser 40 is transmitted to photoreceiver 220 by mirrors (221, 220), through half-wave plate 223, optical isolator 221, and combined with the frequency comb laser at polarizing beam splitter 217 and co-propagated through polarization analyzer 218 and lens 219. The radiofrequency beat frequency between frequency comb 41 and reference laser 40 is transmitted to phase-frequency detector 228, which in combination with a second input radiofrequency signal from a second reference radiofrequency 229 outputs a voltage which is input into the loop filter 227. The output of loop filter 227 activity adjusts reference laser current and temperature controller 226, thus stabilizing reference laser 40 to radiofrequency standard 234 through frequency comb 41. Wavelength meter 78 receives frequency comb 41 or reference laser 40 via mirrors (216, 215) and beam splitter 214. Reference laser 40 laser light is received by fiber-to-free-space collimator 211 via mirrors (212, 213), transmitted over mid-infrared fiber optic 210 and out of a second fiber-to-free-space collimator 209. Reference laser light from 209 is received by half-wave plate 208, mirrors (207, 206) polarization beam splitter 205, polarization analyzer 240, and photoreceiver 235. Laser light from mirror 70 in FIG. 1 is received by mirrors (201, 203), half-wave plate 204, polarization beam splitter 205, polarization analyzer 240, and photoreceiver 235. The radiofrequency beat frequency from photoreceiver 235 is mixed in phase-frequency detector 236 with reference radiofrequency 237 to produce an output voltage transmitted to loop filter 238 whose output actively adjusts the laser current and temperature controller 239 which controls the wavelength of laser 2 from FIG. 1. The now stabilized mid-infrared laser light 8 from FIG. 1 is transmitted to the high finesse optical resonator and sample cell as in FIG. 1.

In the linear absorption spectrometer 100, laser light source 2 provides mid-infrared laser light 4. Mid-infrared light source 2 can be a continuous wave laser, wherein a wavelength of mid-infrared laser light 4 is selected for absorption of radiocarbon in the sample. In a particular embodiment, the wavelength of mid-infrared laser light 4 is selected such that radiocarbon absorbs mid-infrared laser light 4 while other chemical species that may be present in simple cell 24 do not absorb at that wavelength or weakly absorb at that wavelength as compared to the absorption coefficient for radiocarbon. In a certain embodiment, the wavelength of mid-infrared laser light 4 is selected for absorption by radiocarbon in a P-branch in a rovibrational absorption spectrum for radiocarbon, based on a quantum mechanical selection rule for a change in rotational quantum number J, wherein $\Delta J=-1$.

It is contemplated that the wavelength of mid-infrared laser light 4 is from 1 micrometers (µm) to 50 µm, specifically from 1 µm to 30 µm, and more specifically from 2 µm 20 µm. An average power of mid-infrared laser light 4 can be from 1 microwatts (µW) to 10 watts (W), specifically from 100 µW to 100 milliwatts (mW), and more specifically from 1 mW to 30 mW. Moreover, mid-infrared laser light 4 in the high finesse optical resonator comprises a fractional frequency stability that is greater than 1 in $10^8$.

Laser light source 2 can include a semiconductor laser. Exemplary laser light sources 2 include a quantum cascade laser, difference frequency generation laser, fiber laser, optical parametric oscillator, vertical-cavity surface-emitting laser, and the like.

In an embodiment, reference laser light 42 is combined with mid-infrared laser light 2. Reference laser light 42 can include a mid-infrared optical comb. The mid-infrared optical comb can include a fractional frequency instability that is less than 1 in $10^{11}$. A wavelength of the mid-infrared optical comb can be from 1 micrometers (µm) to 50 µm, specifically from 1 µm to 30 µm, and more specifically from 2 µm 20 µm. An average power of the mid-infrared optical comb can be from 1 µW to 10 W, specifically from 100 µW to 100 mW, more specifically from 1 mW to 30 mW.

It is contemplated that mid-infrared optical comb 41 comprises optical cavities, fiber laser oscillators, solid-state laser oscillators, microresonators, saturable absorbers, laser pump diodes, semiconductor lasers phase modulators, intensity modulators, optical amplifiers, optical compressors, nonlinear frequency conversion crystals, nonlinear photonic devices, waveguides, waveplates, highly nonlinear fiber, and the like.

In some embodiments, reference laser 40 is a stabilized frequency reference such as a helium neon laser (HeNe laser). The HeNe laser can include a fractional frequency instability that is less than 1 in $10^{10}$. A wavelength of the HeNe laser can be from 600 nanometers (nm) to 4000 nm, specifically 633 nm. An average power of the HeNe laser can be from 1 µW to 1 W, specifically from 100 µW to 1 mW, more specifically from 100 µW to 2 mW.

Mid-infrared laser light 4 from laser light source 2 is received by optical switch 6. Optical switch 6 modulates mid-infrared laser light 4. Here, modulation of mid-infrared laser light 4 includes intensity modulation, frequency modulation, phase modulation, or a combination thereof. In an embodiment, optical switch 6 modulates a frequency of mid-infrared laser light 4 to produce modulated mid-infrared laser light 4 that are communicated to high finesse optical resonator 10. A repetition rate of modulated mid-infrared laser light 4 produced by optical switch 6 can be from 1 hertz (Hz) to 50 kHz, specifically from 5 hertz (Hz) to 10 kHz, and more specifically from 25 hertz (Hz) to 2 kHz.

Exemplary optical switches include acousto-optic modulators, electro-optic modulators, mechanical switches, fiber optic switches, and the like. In an embodiment, optical switch 6 includes a germanium acousto-optic modulator to modulate mid-infrared laser light 4 at a frequency of 60 MHz.

Figure 6:
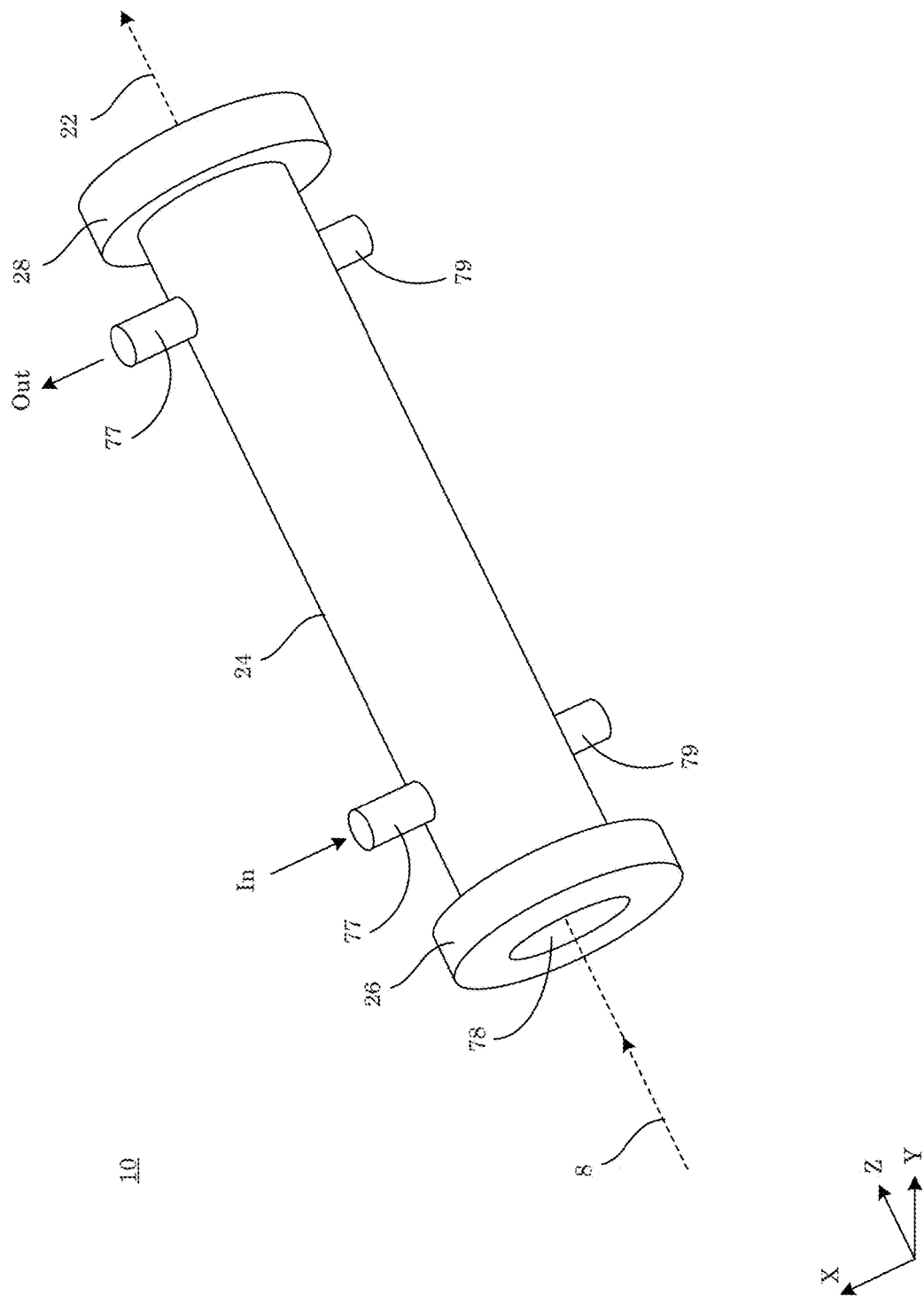
FIG. 6 shows a perspective view of a sample cell.
Figure 7:
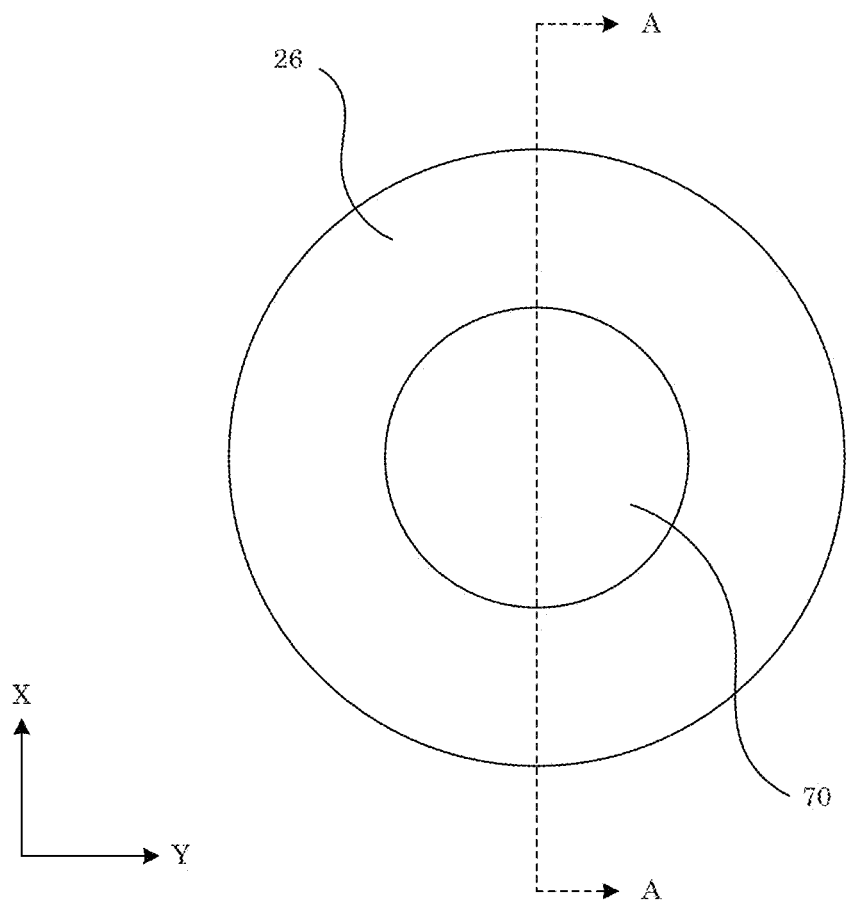
FIG. 7 shows a front view of the sample cell shown in FIG. 6.

High finesse optical resonator 10 receives mid-infrared laser light 8 from optical switch 6, reference laser light 42 from reference laser 40, the sample that includes radiocarbon, a cooling fluid, or a combination thereof. With reference to FIG. 6 (perspective view), FIG. 7 (front view), FIG. 8 (cross-section along line A-A shown in FIG. 7), and FIG. 9 (cross-section along line B-B shown in FIG. 8), high finesse optical resonator 10 includes first optical window, first supermirror 12 disposed on first zero-pressure difference mirror mount 26, second supermirror 16 disposed on second zero-pressure difference mirror mount 28, second optical window, and sample cell 24 interposed between first supermirror 12 and second supermirror 16. High finesse optical resonator 10 has geometric path length L from reflection surface 14 of first supermirror 12 to reflection surface 18 of second supermirror 16. Geometric path length L can be from 10 micrometers (µm) to 1 kilometers (km), specifically from 1 centimeters (cm) to 10 meters (m), and more specifically from 75 cm to 3 m. It is contemplated that mid-infrared laser light 20 propagates along geometric path length L a plurality of times as mid-infrared laser light 20 is reflected a plurality of times between first supermirror 12 and second supermirror 16 to provide an effective path length of high finesse optical resonator 10 an integral number of times over primary path length L. As a result, the effective path length of high finesse optical resonator 10 can be from 1 km to 600 km.

A combination of first supermirror 12, first zero-pressure difference mirror mount 26, second supermirror 16, and second zero-pressure difference mirror mount are selected to provide a high finesse for high finesse optical resonator 10, wherein a reflectivity of first supermirror 12 and second supermirror 16 independently is from 99.9% to 99.99999% at a wavelength of mid-infrared laser light 20. In an embodiment, reference laser light 42 is present with mid-infrared laser light 20 in high finesse optical resonator 10, wherein a reflectivity of first supermirror 12 and second supermirror 16 independently is from 10% to 99.7%, specifically from 50% to 99.7% at a wavelength of reference laser light 40.

First supermirror 12 and second supermirror 16 are selected to transmit and reflect mid-infrared laser light (8, 20, 22). Moreover, first supermirror 12 and second supermirror 16 independently include a radius of curvature that provides cavity ring down reflection in high finesse optical resonator 10. The radius of curvature can be from micrometers (µm) to hundreds of meters (m), specifically from 5 mm to 5 m, and more specifically from 35 cm to 1.5 m. Exemplary supermirrors (12, 16) include alternating dielectric stacks, metallic mirrors, silicon mirrors, calcium fluoride mirrors, zinc selenide mirrors, and the like. Supermirrors (12, 16) can include a plurality of coating layers that provide a selected reflectivity, birefringence, and the like. Second supermirror 16 in combination with first supermirror 12 includes a relative difference of refractive index $\Delta n/n$ from $3\times10^{-11}$ to $3\times10^{-2}$, specifically from $1\times10^{-8}$ to $3\times10^{-4}$, and more specifically from $1\times10^{-8}$ to $6\times10^{-6}$.

Figure 8:
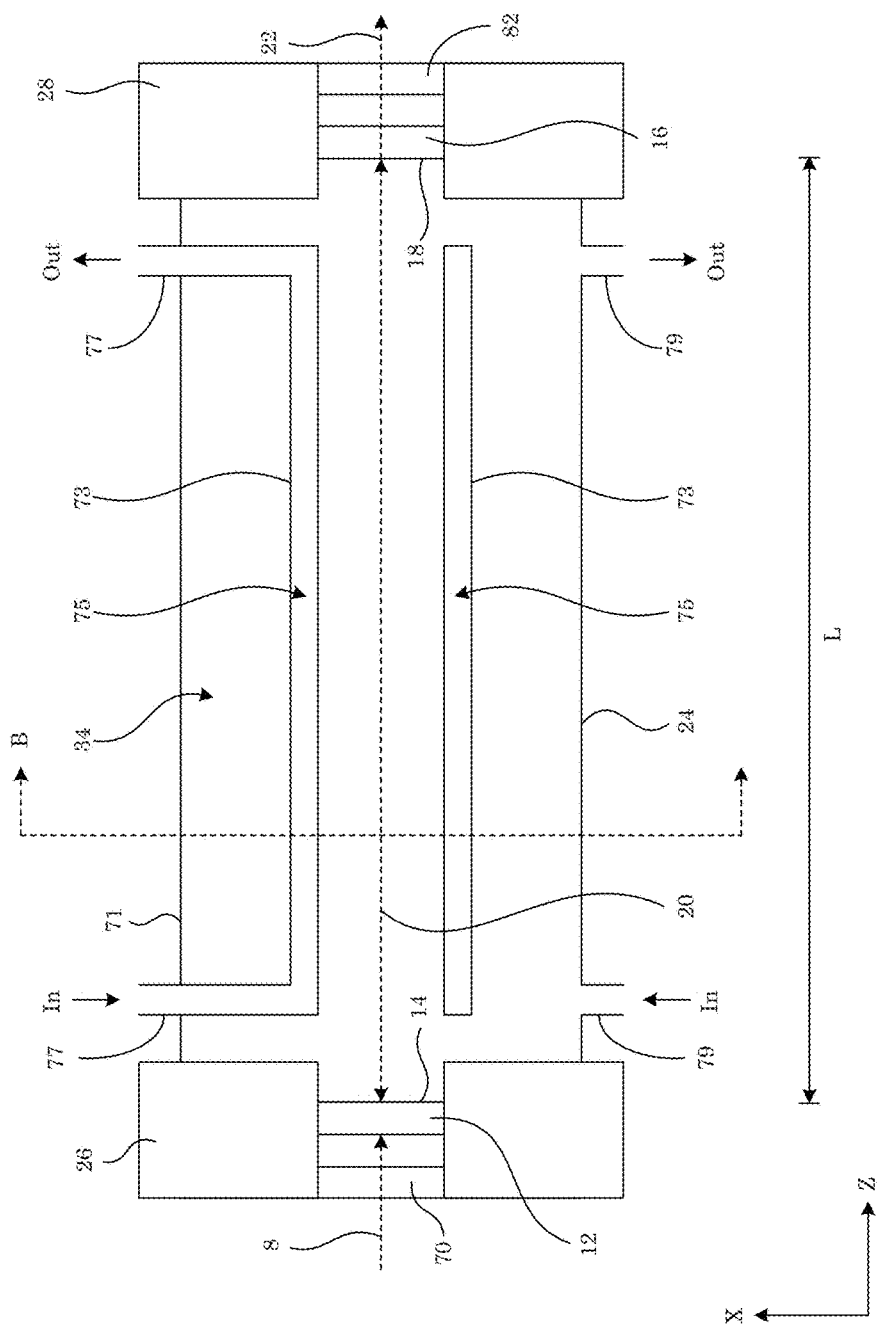
FIG. 8 shows a cross-section along line A-A of the sample cell shown in FIG. 7.
Figure 9:
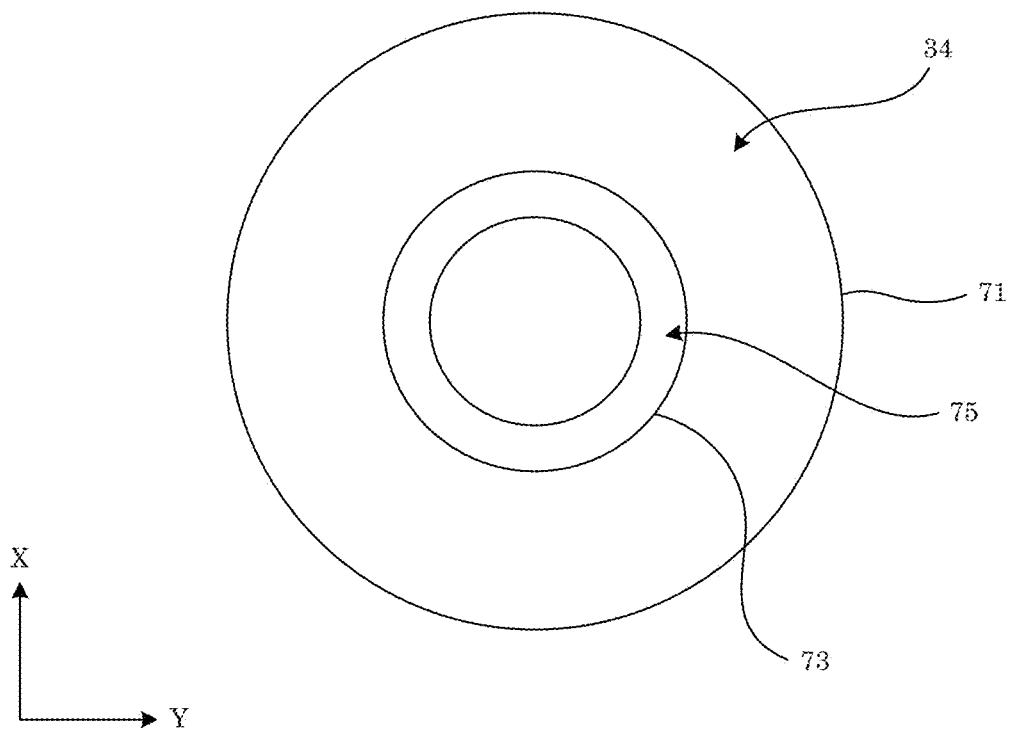
FIG. 9 shows a cross-section along line B-B of the sample cell shown in FIG. 8.

With reference to FIG. 8 (longitudinal cross-section of high finesse optical resonator 10) and FIG. 9 (cross-section along line B-B shown in FIG. 8), sample cell 24 receives the sample that is subject to irradiation by mid infrared laser light 22 as midinfrared laser light 22 propagates a plurality of times along geometric path length L from first super mirror 12 to second super mirror 16. Sample cell includes primary fluid conduit 34 disposed from first supermirror 12 to second supermirror 16 and that receives the sample such that the sample is disposed in primary fluid conduit 34 during linear absorption by the sample. Disposal of the sample in primary fluid conduit 34 of sample cell 24 can occur via ports 79. In this manner, sample cell 24 can be a static sample cell or a flow sample cell with regard to flow of the sample through sample cell 24. Further, sample cell 24 can include secondary fluid conduit 73 disposed in primary fluid conduit 34 to receive a cooling fluid in flow tube 75 introduced via port 77 so that secondary fluid conduit cools sample cell 24 and the sample. As a result, a temperature and pressure of sample cell 24 can be controlled. Accordingly, the pressure of sample cell 24 in a presence of the sample can be from 100 Pascals (Pa) to 133 kilopascals (kPa), specifically from 100 Pa to 10 kPa, and more specifically from 100 Pa to 3 kPa. A temperature of sample cell 24 can be from 2 Kelvin (K) to 330 K, specifically from 150 K to 300 K, and more specifically from 180 K, to 220 K.

In an embodiment, secondary fluid conduit 73 is isolated from fluid communication with primary fluid conduit 34, wherein the sample is present in an absence of contact with the cooling fluid. In some embodiments, secondary fluid conduit 73 is in fluid communication with primary fluid conduit 34, wherein the sample can be combined with the cooling fluid.

Figure 10:
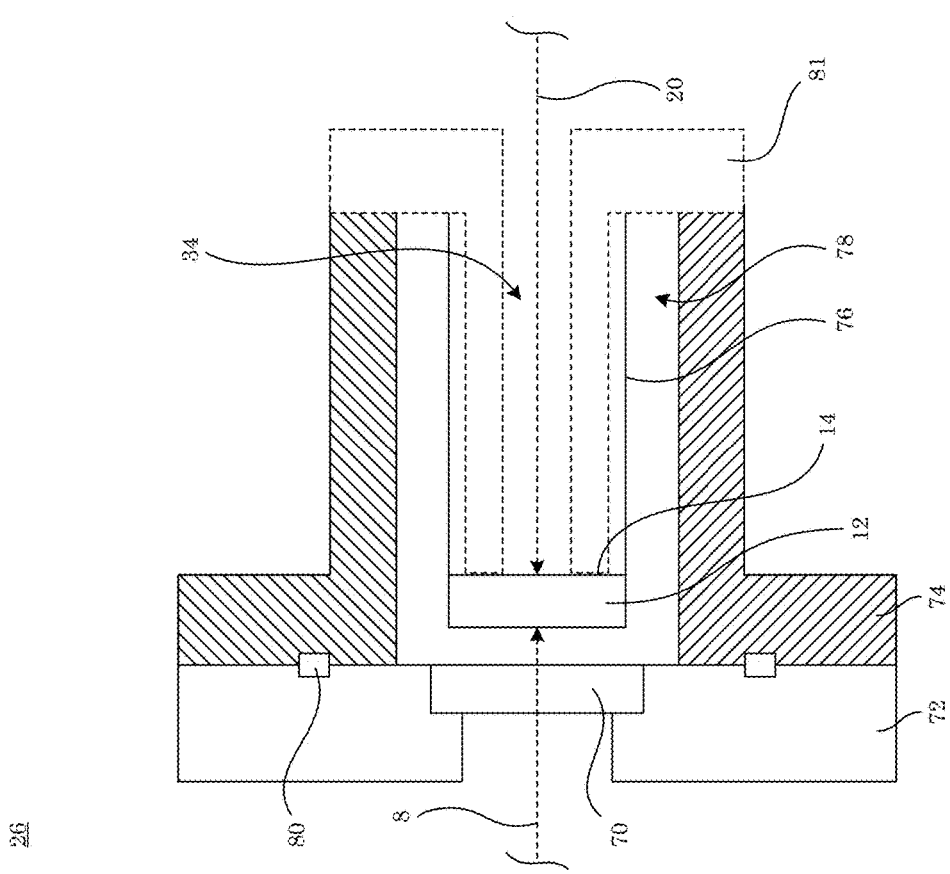
FIG. 10 shows a cross-section of a zero-pressure difference mirror mount.

Supermirror (12, 16) is disposed in zero-pressure difference mirror mount (26, 28). In this manner, supermirrors (12, 16) are not subjected to strain such that the respective birefringence of supermirrors (12, 16) are maintained without variation when disposed in zero-pressure difference mirror mounts (26, 28) or subjected to a change in pressure of sample cell 24. With reference to FIG. 10, first zero-pressure difference mirror mount 26 can include flange 74 connected to bellows 76 wherein first optical window and first supermirror 12 are disposed on an end of bellows 76 opposite piezoelectric transducer member 81. Piezoelectric member 81 changes primary path length L of high finesse optical resonator 10 by lengthening or shortening links of bellows 76 to change a position of first super mirror 12 relative to second super mirror 16. Flange 72 is disposed on flange 74 and form a vacuum and pressure seal with sample cell 24 to maintain a pressure therein, wherein interior 78 between bellows 76 and flange 74 is in fluid communication with interior 34 of sample cell 24. Seal 80 (e.g., a gasket such as an elastomer or metal) can be disposed between flanges 72 and 74 for sealing. Flanges (72, 74) independently can have a flat face, a gland, a knife-edge provision, and the like to provide the ceiling service therebetween. In this configuration, first super mirror 12 is strain-free, while optical window 70 can be subjected to strain due to a pressure differential across optical window 70. A shape of flanges, optical window 70, and first super mirror 12 orthogonal to the plane of the view in FIG. 10 can be any shape effective for linear absorption of the sample in a presence of midinfrared laser light 20 and can be, e.g., circular, polygonal, square, rectangular, ellipsoidal, and the like.

Figure 11:
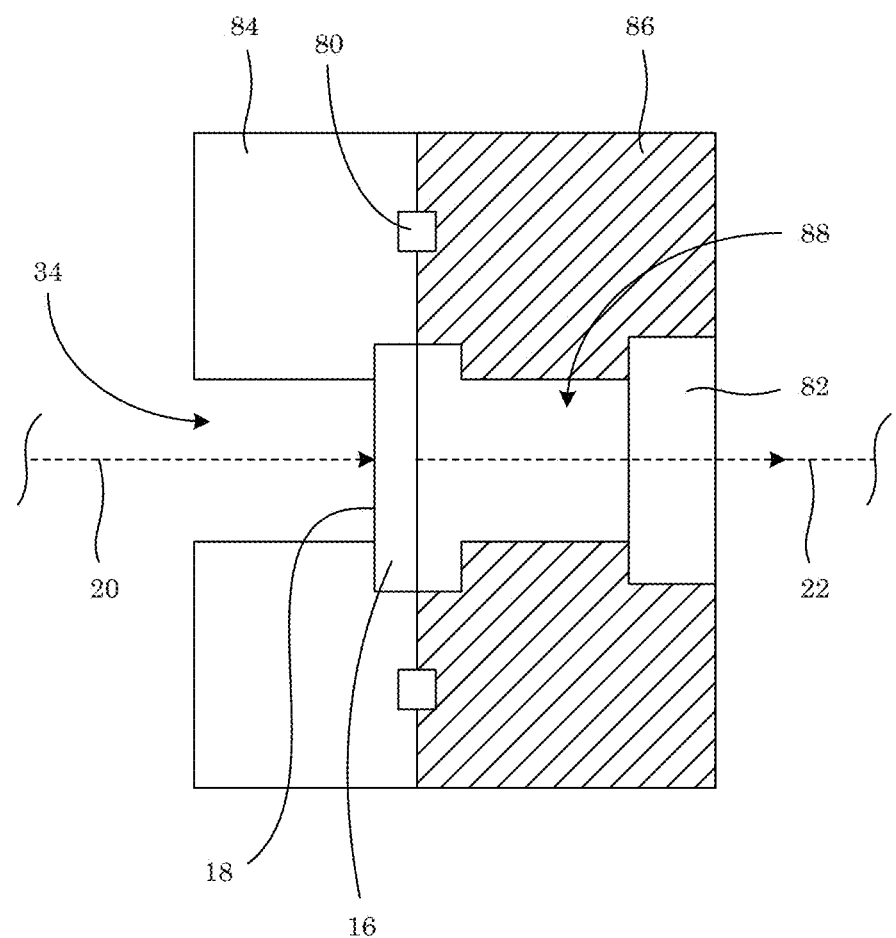
FIG. 11 shows a cross-section of a zero-pressure difference mirror mount.

With reference to FIG. 11, second zero-pressure difference mirror mount 28 can include flange 84 that receives second super mirror 16. Flange 86 is disposed on flanged 84 and receives optical window 82. Optical window 82 and flange 86 form a vacuum and pressure seal with sample cell 24 to maintain a pressure therein in combination with flange 80 and optical window 70 of first zero-pressure difference mirror mount 26. Seal 80 can be disposed between flanges 84 and 86 for sealing. Flanges (84, 86) independently can have a flat face, a gland, a knife edge provision, and the like to provide the ceiling service therebetween. In this configuration, second super mirror 16 is strain-free, while optical window 82 can be subjected to strain due to a pressure differential across optical window 82. A shape of flanges, optical window 82, and second super mirror 16 orthogonal to the plane of the view in FIG. 11 can be any shape effective for linear absorption of the sample in a presence of midinfrared laser light 20 and can be, e.g., circular, polygonal, square, rectangular, ellipsoidal, and the like.

Figure 12:
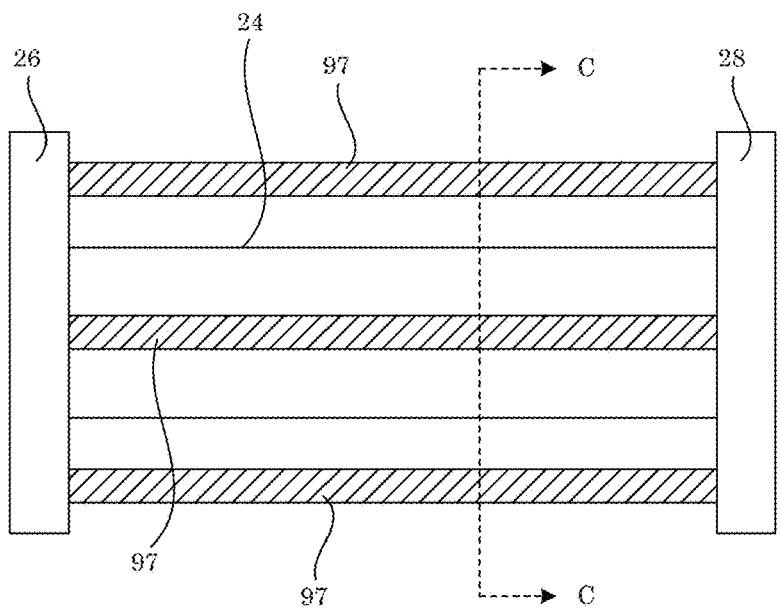
FIG. 12 shows a side view of a high finesse optical resonator in panel A, and panel B shows a cross-section along line C-C of the optical resonator shown in panel A.
Figure 12:
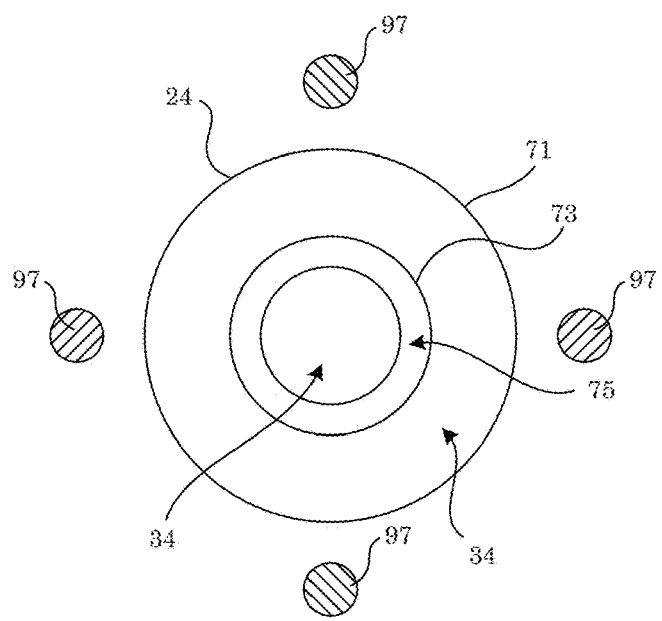

It is contemplated that linear absorption spectrometer 100 provides frequency stabilization of mid infrared laser light (8, 20, 22). The frequency stabilization of mid infrared laser light (8, 20, 22) can be accomplished mechanically, electronically, optically (e.g., see FIG. 3, FIG. 4, or FIG. 5), and the like. According to an embodiment, with reference to FIG. 12, frequency stabilization of mid infrared laser light 20 occurs via mechanical stabilization of high finesse optical resonator 10, wherein high finesse optical resonator 10 includes spacer member 97 to space apart first zero-pressure difference mirror mount 26 the second zero-pressure difference mirror mount 28. Here, spacer member 97 maintains a substantially constant distance of separation between zero-pressure difference mirror mounts (26, 28). Spacer member 97 can have an elongation length stability from 5 parts per million (ppm) to 1 part per quadrillion (ppq), specifically from 100 ppm to 1 part per trillion (ppt), and more specifically from 100 ppm to 10 ppt, and a temperature from 2 K to 330 K, specifically from 150 K to 310 K, more specifically from 290 K to 300 K. It is contemplated that spacer member 97 can have a coefficient of thermal expansion with absolute values from $1\times10^{-11}$ K$^{-1}$ to $1\times10^{-5}$ K$^{-1}$, specifically from $1\times10^{-9}$ K$^{-1}$ to $1\times10^{-6}$ K$^{-1}$, and more specifically from $1\times10^{-9}$ K$^{-1}$ to $1\times10^{-7}$ K$^{-1}$.

A number (e.g., 1, 2, 3, or more) of spacer members 97 can be selected to stabilize high finesse optical resonator 10 and can be used for alignment thereof. A cross-sectional shape of spacer member 97 can be any shape effective for mechanical stabilization and can be, e.g., circular, polygonal, square, rectangular, ellipsoidal, and the like. Exemplary materials for spacer member 97 include low coefficient of thermal expansion plastic, glass, composite, ceramic, metal, or a combination thereof, and the like. In an embodiment, spacer member 97 includes a low coefficient of thermal expansion alloy such as iron-nickel (available under the tradename INVAR). A length of spacer member 97 can be from 10 µm to 1 km, specifically from 1 cm to 10 m, and more specifically from 75 cm to 3 m.

In linear absorption spectrometer 100, the sample is disposed in sample cell 24 of high finesse optical resonator 10 and subjected to radiation by midinfrared laser light 20. In an embodiment, the sample includes a gas. The gas can be from a petrogenic source, biogenic source, medical source, radioactive source, and the like, or a combination thereof. The sample can include radiocarbon, and the radiocarbon absorbs midinfrared laser light 20. As used herein, "radiocarbon" refers to carbon-14 ($^{14}$C). Exemplary species that include radiocarbon in the sample include an inorganic oxide (e.g., $CO_2$, CO and the like), a hydrocarbon (e.g., an alkane such as methane, an alkene such as ethylene, an alkyne such as acetylene, and the like), a hydrocarbon (e.g., an organic acid such as acetic acid, formic acid, and the like), an ether, an ester, a ketone, and the like. It should be appreciated that carbon in the sample can include radiocarbon alone or in combination with carbon-12 ($^{12}C$) or carbon-13 ($^{13}C$).

Other species present in the sample can include an atom or molecule that include a nitrogen, oxygen, phosphorus, sulfur, and the like. Exemplary contaminant species in the sample include a phosphorus oxide (e.g., $P_xO_y$, wherein x and y are integers and independently can be 0, 1, 2, and the like), nitrogen oxides ($N_xO_y$, wherein x and y are integers and independently can be 0, 1, 2, and the like), sulfur oxides ($S_xO_y$, wherein x and y are integers and independently can be 0, 1, 2, and the like), and the like.

Radiocarbon can be present in the sample from 100 attomol per mol (amol/mol) to 10 micromole (μmol/mol), and more specifically from 100 amol/mol to 10 pmol/mol, based on a total number of moles in the sample. It is contemplated that the absolute mole fraction of the radiocarbon in the sample is from 1 parts-per-quadrillion (ppq) to 2.5 parts-per-trillion (ppt).

The sample can be cooled via thermal transfer with the sample when cooling member 73 of sample cell 24. The cooling fluid disposed in coolant reservoir 75 of cooling member 73 can have a temperature from 2 K to 330 K, specifically from 150 K to 300 K, and more specifically from 180 K to 220 K. Exemplary cooling fluids include helium, nitrogen, ethylene glycol, nanofluids, polydimethylsiloxaneor a combination thereof, and the like.

Cavity ring down light 22 is produced in response to absorption of mid infrared laser light 20 by the sample. Photo receiver 30 receives cavity ring down light 22 from high finesse optical resonator 10 and produces absorption signal 32. Photo receiver 30 can be followed a photodiode, photomultiplier, photodiode array, thermopile, and the like. In an embodiment, photo receiver 30 includes the photodiode and electronic amplifiers and filters. It is contemplated that photo receiver 30 is cooled to a temperature at which photo receiver 30 noise equivalent power is less than five times a shot noise limit of cavity ring down laser light 22. In this manner, photo receiver 30 that is sensitively requires cavity ring down light 22. It is contemplated that photoreceiver 30 is arranged to provide an etalon-immune distance. As used herein, "etalon-immune distance" refers to a distance from the second supermirror reflective surface 18 to photo receiver 30 that is an integer multiple of distance from the second supermirror reflective surface 18 to first supermirror reflective surface 14.

In an embodiment, a process for making linear absorption spectrometer 100 includes providing laser light source 2; disposing optical switch 6 in optical communication with laser light source 2; providing high finesse optical resonator 10 in optical communication with optical switch 6 to receive mid infrared laser light 8 modulated by optical switch 6; and disposing photo receiver 30 in optical communication with high finesse optical resonator 10 to receive cavity ring down light 22 therefrom. Here, the process also can include disposing first super mirror 12 in first zero-pressure difference mirror mount 26; disposing second super mirror 16 in second zero-pressure difference mirror mount 28; disposing first zero-pressure difference mirror mount 26 on sample cell 24; and disposing second zero-pressure difference mirror mount 28 on sample cell 24.

Linear absorption spectrometer 100 has numerous beneficial uses, including performing linear absorption spectrometry on a sample, determining an absolute mole fraction and number density of radiocarbon in the sample, and the like. In an embodiment, a process for determining an absolute mole fraction and number density of radiocarbon in the sample includes adjusting the wavelength of mid-infrared laser light 4 to be transmitted by linear absorption spectrometer 100 and probing radiocarbon absorption; measuring midinfrared laser frequency by referencing to mid-infrared optical frequency comb 41 or the like; measuring the decay signal of midinfrared laser light 8 exiting linear absorption spectrometer 100 using photoreceiver 30 and digitizer 108; determining the decay rate by fitting exponential decay plus baseline offset model to measured decay signal; repeating decay rate measurement a plurality of times to improve measurement precision; repeating absolute laser frequency and cavity ring-down decay rate measurements over multiple wavelengths yielding spectrum of base cavity losses plus absorption losses; fitting parameterized, mathematical model of the absorption spectrum to the measured spectrum to yield peak area associated with midinfrared light absorption by radiocarbon, treating the spectrum as a linear superposition of base spectrometer losses having a constant, linear or quadratic wavelength dependence with residual, sinusoidal features caused by parasitic coupled-cavity effects (etalons), an absorption line profile for radiocarbon centered on radiocarbon transition frequency, additional line profiles of interfering species; calculating number density of the radiocarbon as ratio of fitted peak area for radiocarbon to line intensity of radiocarbon transition evaluated at sample temperature; calculating molar fraction of radiocarbon by dividing radiocarbon number density by sample number density based on measured sample pressure and temperature.

Linear absorption spectrometer 100 has numerous advantageous and beneficial properties. In an aspect, linear absorption spectrometer 100 provides ultrasensitive detection of modern levels (e.g., less than 2 ppt) of radiocarbon in the sample. Moreover, linear absorption spectrometer 100 overcomes presence of parasitic etalons because etalons have been minimized by of optical element materials, coatings, and relative position of normal-incidence optics, photoreceiver and the like. Further, averaging of spectra provides reduction in effect due to randomly varying etalons. Additionally, linear absorption spectrometer 100 includes simple cell 24 with cooling member 73 to provide an ultralow temperature to the sample to reduce spectral congestion due to contaminants in the sample.

The articles and processes herein are illustrated further by the following Examples, which are non-limiting.

EXAMPLES

Example 1. Linear Absorption Spectrometer for Trace Detection of Radiocarbon

Optical detection of radiocarbon via linear absorption below contemporary levels was performed by cavity ring-down spectroscopy in the linear absorption spectrometer. Petrogenic and biogenic samples of $CO_2$ were distinguished by optical measurements.

Sub-picomole per mole (pmol/mol) detection of radiocarbon in samples of $CO_2$ originating from the combustion of either petrogenic (i.e. fossil fuel) or biogenic samples was performed with a low-temperature (T=220K) cavity ring-down spectrometer pumped by a quantum cascade laser.

Repeated spectroscopic measurements of a representative 86% biogenic sample yielded a standard error of 130 fmol/mol (1 part-per-quadrillion, or ppq, is defined as 1 fmol/mol) in two hours of laboratory time. Multi-hour measurements repeated over several days showed a standard deviation of 60 fmol/mol, thus validating the potential for high-fidelity optical detection using linear absorption spectroscopy.

The mid-infrared cavity ring-down spectrometer included a continuous-wave (cw) quantum cascade laser (QCL), an acousto-optic modulator (AOM) to act as a fast optical switch, a high-finesse (F=50000) optical resonator whose axis resides at the cross-hairs of a cylindrical cold finger, and a liquid-nitrogen-cooled InSb photoreceiver. Cavity time constants τ were digitized and fit at rates≈100 Hz with an electronic bandwidth of 500 kHz using a low-bandwidth transmission lock of the laser to a given cavity mode. Molecular spectra were acquired by tuning the QCL current and thus discretely jumping the laser frequency from one mode of the optical resonator to another mode. With a cavity free spectral range of FSR≈100 MHz, 1.1 GHz-wide spectra of $CO_2$ were recorded in approximately 70 s. The spectral sampling grid defined by the optical resonator length was shifted in sub-FSR increments by tuning a piezo-electric transducer mounted to one of the cavity mirrors.

Figure 13:
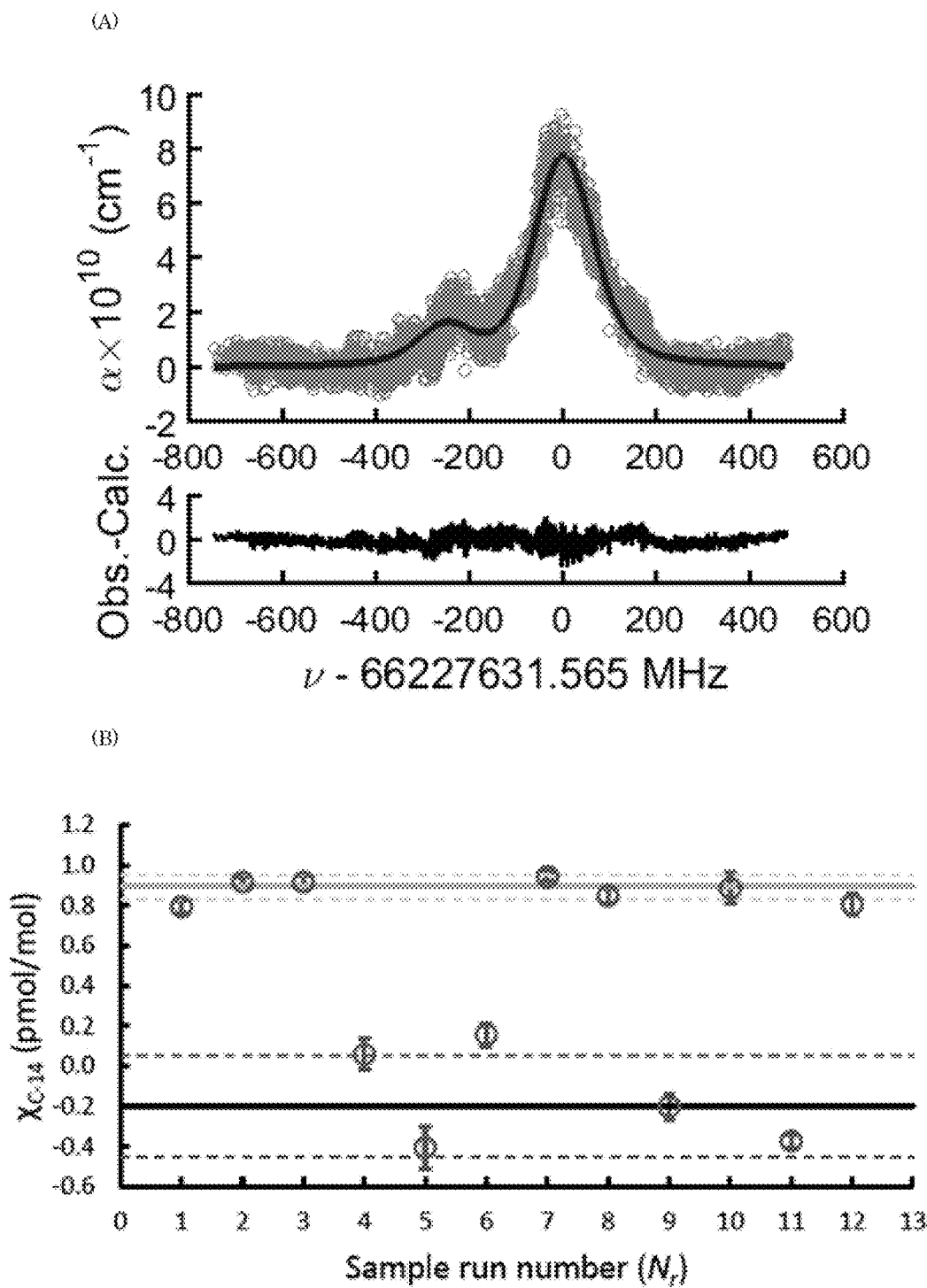
FIG. 13 (panel A) shows a plot of 500 interleaved, baseline-corrected spectra (gray circles) of 86% biogenic $CO_2$ recorded in less than 10 hours. From the interleaved residuals in the bottom panel (black line), the minimum detectable absorption coefficient is $\alpha_{min}=5.4\times 10^{-11}$ cm$^{-1}$, and panel b shows a fit of $\chi_{C-14}$ for repeated runs (1-10 hours per run) of either the 86% biogenic sample (green solid and dashed lines) or 0% biogenic (anthropogenic) sample (black solid and gray dashed lines) according to Example 1.

A representative compilation of interleaved, baseline-corrected spectra is shown in panel A of FIG. 13. Each one of the 500 spectra (gray dots) were individually fit by a model comprising two transitions with Voigt line shapes separated by a known relative frequency along with a quadratic baseline function. The more intense transition in panel A of FIG. 13 was a $^{13}CO_2$ transition with a strong temperature dependence.

Panel B of FIG. 13 shows results of repeated sample runs (red open circles). Error bars are $\pm 1\sigma_{C-14}$, where $\sigma_{C-14}$ is the standard error associated with the sample run. For the 86% biogenic sample runs, the weighted average $\chi_{C-14}$=890 fmol/mol and $\pm 1\sigma_{C-14}$=60 fmol/mol bounds are plotted as solid and dashed green lines, respectively. For the 0% biogenic (i.e., petrogenic) sample runs, $\chi_{C-14}$=−200 fmol/mol and $\pm 1\sigma_{C-14}$=250 fmol/mol bounds are plotted as solid black and dashed gray lines, respectively. The larger scatter in the retrieved $\chi_{C-14}$ values for the petrogenic sample runs as compared to the 86% biogenic sample runs is indicative of a systematic effect traceable to run-to-run baseline drifts and underscores the current need for repeated long-duration sample runs. Applying the physical constraint $\chi_{C-14} \geq 0$ yields a slightly different weighted mean for the petrogenic sample of $\chi_{C-14}$=220±50 fmol/mol. The optical detection of radiocarbon in the gas-phase sample of 86% biogenic $CO_2$ and a precision of 60 fmol/mol, a value well below contemporary ambient levels.

Example 2. Ultra-Sensitive Cavity Ring-Down Spectroscopy in the Mid-Infrared Spectral Region An ultra-sensitive cavity ring-down spectrometer which operates in the mid-infrared spectral region near 4.5 μm was constructed in used to acquire a noise-equivalent absorption coefficient of $2.6 \times 10^{-11}$ cm$^{-1}$ Hz$^{-1/2}$ with less than 150 nW of optical power incident on a photodetector. Quantum noise was observed in the individual ring-down decay events, leading to quantum-noise-limited short-time performance. A combination of high sensitivity and robustness make it well suited for measurements of ultra-trace gas species as well as applications in optics and fundamental physics.

Cavity ringdown spectroscopy (CRDS) is a cavity-enhanced technique in which a high finesse Fabry-Pérot cavity is used to achieve a long path length (10's of km to 100's of km). During a CRDS measurement the cavity is first optically pumped by the laser source. This light is then extinguished and the corresponding passive decay of the intracavity optical power is monitored. The exponential decay time, the ring-down time constant (τ), is directly related to the absorption, α, within the cavity:

$$\alpha = \frac{1}{c\tau} - \frac{1}{c\tau_0}, \qquad (1)$$

wherein c is the speed of light and $\tau_0$ is the empty-cavity ring-down time constant which accounts for mirror losses due to transmission, absorption, and scattering. CRDS is insensitive to laser amplitude fluctuations.

Figure 14:
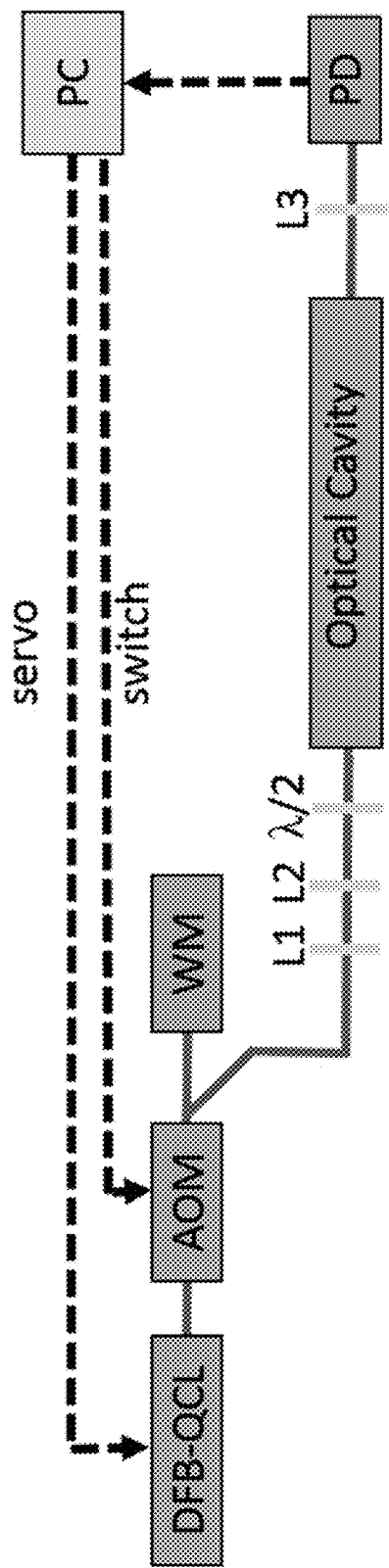
FIG. 14 shows, according to Example 2, a distributed-feedback quantum cascade laser (DFB-QCL) that provides the infrared radiation. An acousto-optic modulator (AOM) is used as a fast optical switch to initiate the ring-down decay events. Also shown are a wavelength meter (WM), lenses (L1-L3), a half-wave plate ($\lambda/2$), and the InSb photodetector (PD). The DFB-QCL is actively stabilized to a given cavity mode via a low frequency transmission lock implemented using custom software and a personal computer (PC)
Figure 15:
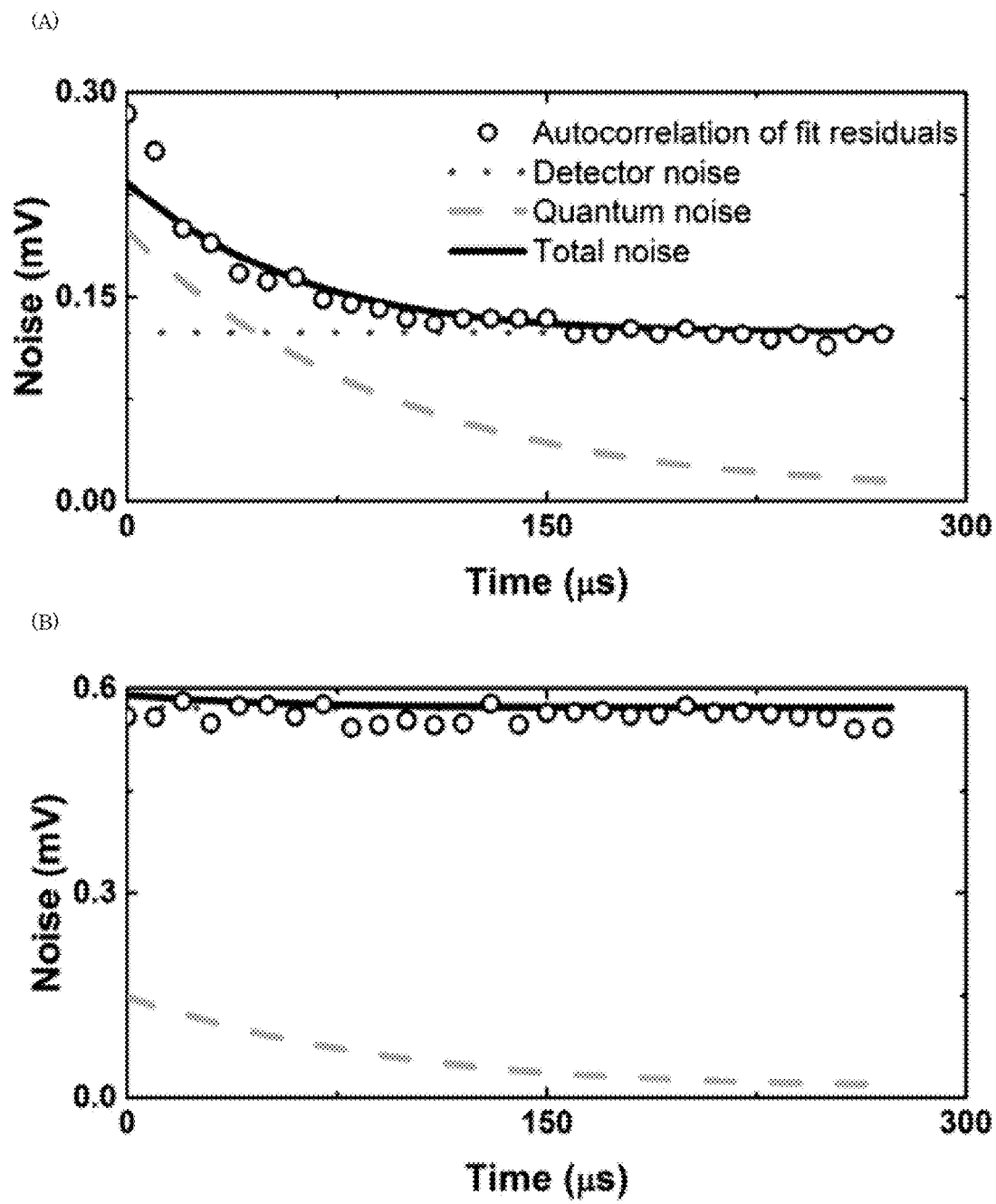
FIG. 15 shows, according to Example 2, an autocorrelation of the fit residuals from an ensemble of 720 individually fitted, ring-down decay events. Also shown are calculated detector noise, quantum noise, and total noise curves. Data shown in pane A was recorded with a low-noise InSb photodetector with a measured NEP of 70 fW Hz$^{-1/2}$. The measured ring-down decay events deviate from the detector noise limit for more than 3 time constants and are quantum-noise-limited for a fraction of the decay event. Data shown in panel B was recorded with a noisier InSb photodetector having an R of 3.4 A/W, a G of $10^6$ V/A, and a measured NEP of 320 fW Hz$^{-1/2}$.

While CRDS is routinely performed in the near-infrared, working in the mid-infrared spectral region can be far more challenging due to generally lower component performance and higher component costs. Importantly, supermirror coatings are more difficult to produce in the mid-infrared, leading to much higher absorption and scattering losses. These significant losses lead to far lower build-up of optical power within the cavity and correspondingly lower optical transmission. As a result, very low noise photodetectors are used to achieve high signal-to-noise ratios on the ring-down decay events. In addition, high efficiency electro-optic modulators are not available in the mid-infrared A schematic of the cavity ring-down spectrometer is shown in FIG. 14. Measurements were made with a distributed-feedback quantum cascade laser (DFB-QCL) having a maximum output power of 38 mW and a tuning range of 2205 cm$^{-1}$ to 2213 cm$^{-1}$. The resulting mid-infrared radiation was passed through an optical isolator and then a germanium acousto-optic modulator (AOM). This AOM was used as a fast optical switch to initiate the ring-down decays and to further prevent optical feedback to the laser. The optical extinction was improved by simultaneously chirping the laser frequency away from a given cavity resonance via a change in the DFB-QCL drive current. The $1^{st}$-order output of the AOM was sent through mode-matching optics, a half-wave plate, and then into the optical resonator, while the $0^{th}$-order output was launched into a wavelength meter. Typically, 12 mW of optical power was incident on the cavity input mirror. The half-wave plate was placed before the cavity to reduce the effects of mirror birefringence. This led to a roughly factor of two improvement in sensitivity.

The optical resonator had a nominal length of 1.5 m and a corresponding free spectral range of 100 MHz. The ring-down mirrors had a radius of curvature of 1 m and a power reflectivity of 99.99% leading to a finesse of 31 000 and an effective path length of 15 km. We estimate that the cavity mode matching efficiency was >90%. The ring-down decays were recorded on a 0.1 mm diameter liquid-nitrogen-cooled InSb photodetector with a field of view of 60°, a responsivity of 3.7 A/W, a trans impedance gain of $10^6$ V/A, and a measured noise-equivalent power of 70 fW Hz$^{-1/2}$ and digitized at 1 M Samples s$^{-1}$ by a 22-bit acquisition board. The 3-dB bandwidth of the acquisition board was measured to be B=480 kHz. Given its high bit depth, the digitizer board did not contribute significantly to the overall technical noise. The laser was stabilized to the optical resonator via a low bandwidth (4 Hz) transmission lock which actuated the laser current. Spectral scanning was performed by stepping the laser temperature in increments of the cavity's free spectral range.

The expected root-mean-square (RMS) noise on a given ring-down decay event, $\sigma_V(t)$ is a combination of two-sided quantum and technical sources as follows $$\sigma_V(t) = \sqrt{\frac{eGV(t)}{2\Delta t} + \sigma_{tech}^2} \qquad (2)$$

wherein e is the electron charge, G is the trans impedance gain, V(t) is the observed ring-down signal amplitude, and $\Delta t$ is the sampling interval.

The technical noise is given by $\sigma_{tech}=(NEP/\sqrt{2})RG\sqrt{B}$, where NEP is the one-sided detector noise-equivalent power, R is the detector responsivity, and B is the electronic bandwidth. The quantum noise component scales as the square-root of the signal amplitude while the technical noise component is constant.

The noise within each decay event can be measured by applying the Wiener-Khintchine theorem, in which we equate the noise power spectral density $\sigma_{V,d}^2(f)$ (V²/Hz) to the Fourier transform of the autocorrelation function of the fit residual $r(t)=V(t)-V_{fit}(t)$. Here f is the Fourier frequency and $V_{fit}(t)$ is an exponential fit to the decay signal. Symbolically, $$\sigma_{V,d}^2(f) = 2\int_{-\infty}^{\infty}\left[\frac{1}{T}\sum_{-\frac{T}{2}}^{\frac{T}{2}} r(t)r(t+t')dt\right]e^{-i2\pi f t'}dt' \qquad (3)$$

from which the integrated noise power (variance) can be found as:

$$\sigma_V^2 = \int_0^{\infty} \sigma_{V,d}^2(f)df \qquad (4)$$

Equations (3) and (4) were evaluated using discrete summations for the autocorrelation and Fourier transform. To measure the time dependence of the noise power spectral density, $\sigma_V^2,(f)$ was computed for averaging bins of width $T \ll \tau$ and at times $t_i$ relative to the beginning of the fitting window. In the absence of correlation, Eqs. (3) and (4) yield the variance of the residual signal within an averaging bin.

The signal noise was also measured by analyzing the distribution of fit residuals for an ensemble of decays. For each time $t_j$ relative to the beginning of the fit window, the noise power was given by the variance in the ensemble of residuals. The time-dependent noise calculated in this manner was in good agreement with the single-shot analysis described above, indicating that the noise behaves ergodically. Both approaches yield quantum-noise-limited results which are consistent with Eq. (2), and which decay exponentially with a time constant of $\tau/2$ until the technical noise floor is reached. The agreement between the autocorrelation of the fit residuals and Eq. (2) can be observed in FIG. 2.

In the quantum noise limit (QNL) the relative standard uncertainty in the determination of $\tau$ from an individual fit to a decay event is given by the inverse of the square root of the number of photoelectrons:

$$\left(\frac{\sigma_\tau}{\tau}\right)_{QNL} = \sqrt{\frac{eG}{V(0)\tau}}. \qquad (5)$$

While in the technical noise limit (TNL) the relative standard uncertainty in $\tau$ is given by:

$$\left(\frac{\sigma_\tau}{\tau}\right)_{TNL} = \frac{2\sqrt{2}\,\sigma_{tech}}{V(0)\sqrt{B\tau}}. \qquad (6)$$

The quadrature sum of these two expressions can then be used to approximate the relative uncertainty in the regime where both quantum noise and technical noise are considerable. From Eqs. (5) and (6), the expected quantum-noise-limited and technical-noise-limited (i.e. detector limited) single-decay-event fit uncertainties were 0.008% and 0.015%, respectively, where V(0)=0.50(06) V (corresponding to 136(16) nW). Adding these uncertainties in quadrature yields an approximate total expected fit uncertainty of 0.017%. Experimentally, average fit uncertainties were 0.019%. A typical 1 s ensemble of ring-down time constants (i.e. the first 30 time constants from FIG. 16) have a standard deviation of 0.023%, thus, demonstrating that shot-to-shot fluctuations in the system are minimal.

The presence of quantum noise during a significant fraction of the cavity decays necessitates the use of a weighted least-squares fit with weighting factors $w(t)=1/\sigma_V(t)^2$, where $\sigma_V(t)$ is calculated from Eq. (2). An estimate of the proper weighting factors for any given ensemble requires V(t), which is approximated by the average fit of the first 10 cavity decay events using equal weights. When fitting the portion of each cavity decay that exhibits significant quantum noise (t<100 µs), equal weighting of the data yields an average fit uncertainty that is 20% higher than that observed with proper weighting. Each cavity decay event has a relatively constant offset arising from dark current in the InSb photodetector. For the purpose of calculating w(t), this dark-current offset has been subtracted from V(t) to ensure that the quantum noise contribution to Eq. (2) is not overestimated.

Figure 16:
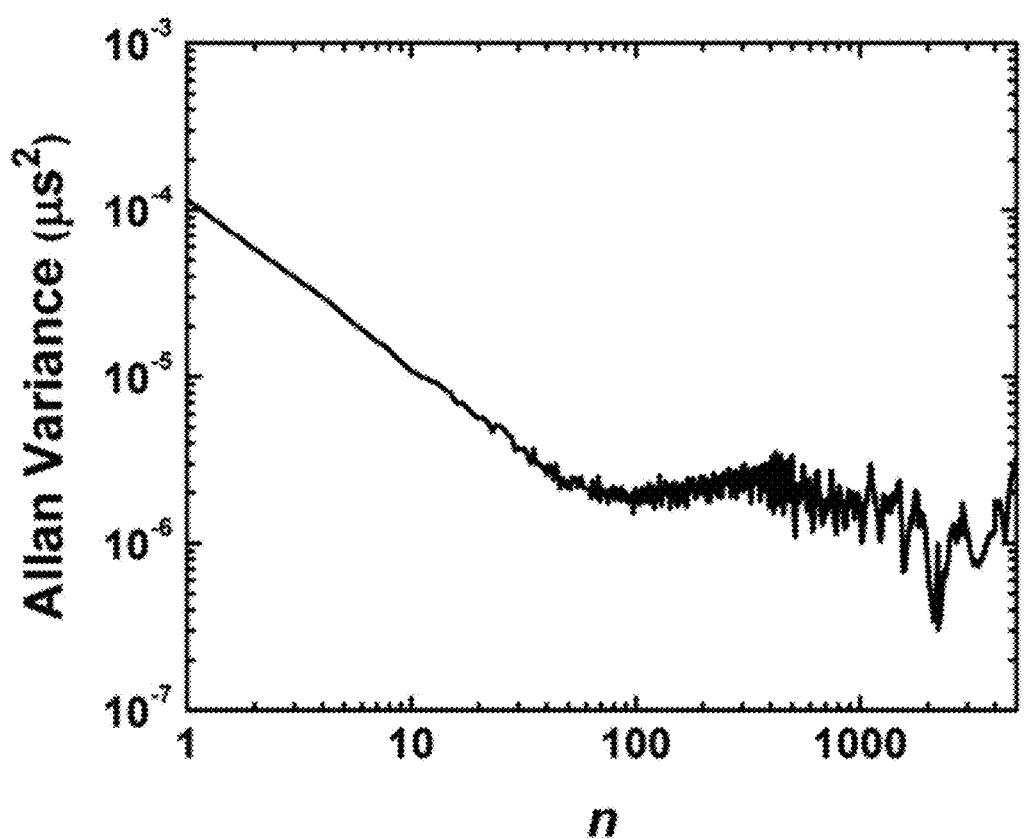
FIG. 16 shows, according to Example 2, a representative Allan variance for the cavity ring-down spectrometer. After 40 acquisitions (1.3 s), a minimum detectable absorption of $2.3\times 10^{-11}$ cm$^{-1}$ and a noise-equivalent absorption coefficient of $2.6\times 10^{-11}$ cm$^{-1}$ Hz$^{-1/2}$ were obtained.

An Allan variance plot, which is a measure of the system stability, can be found in FIG. 16. Based upon this plot we can determine after an optimal averaging time of 1.3 s (corresponding to 40 ring-down decay events) we can achieve a minimum detectable absorption of $2.3\times10^{-11}$ cm$^{-1}$ which corresponds to a noise-equivalent absorption coefficient of $2.6\times10^{-11}$ cm$^{-1}$ Hz$^{-1/2}$. A representative spectrum of a low hydrocarbon air sample can be found in FIG. 17, with absorption noise of $1.6\times10^{-10}$ cm$^{-1}$ (which is within a factor of 4 of the value predicted by the Allan variance in FIG. 16). Based upon this spectrum, a detection sensitivity for $N_2O$ was estimated as 2 pmol/mol with only ten ring-down time constants averaged at each spectral point.

Figure 17:
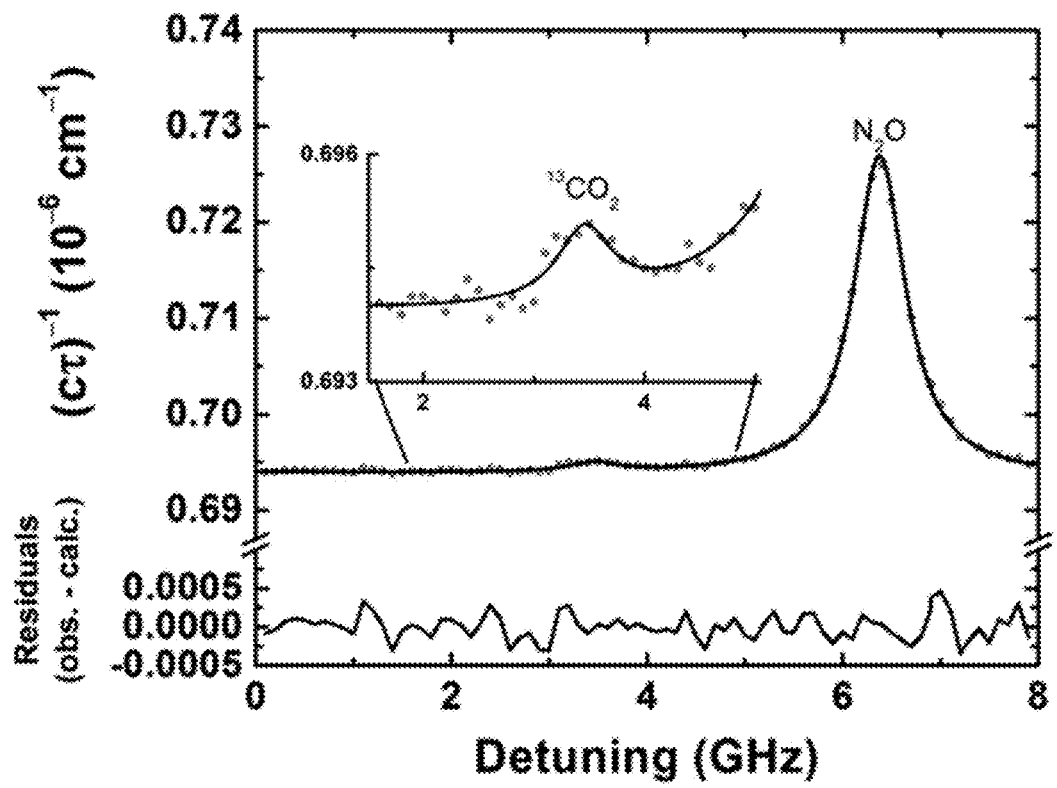
FIG. 17 shows, according to Example 2, an absorption spectrum of 13.3 kPa of zero (low hydrocarbon) air containing 400 pmol/mol of $N_2O$ and 20 nmol/mol of $^{13}CO_2$. The two shown absorption features are the $(0001)\leftarrow(0000)$ P18e $N_2O$ transition at 2207.620380 cm$^{-1}$ with an intensity of $9.072\times 10^{-19}$ cm molec.$^{-1}$ and the $(00011)\leftarrow(00001)$ P76e $^{13}CO_2$ transition at 2207.523521 cm$^{-1}$ with an intensity of $4.239\times 10^{-24}$ cm molec.$^{-1}$. The peak signal-to-noise ratio for the N$_2$O transition is 200:1. Ten ring-down time constants were averaged per spectral frequency. The entire spectrum was recorded in 15 minutes.

With reference to FIG. 17, at a signal-to-noise ratio of 10:1, a weak $^{13}CO_2$ rotational-vibrational transition originating with a rotational quantum number, J, of 76. This measurement of $^{13}CO_2$ in natural abundance was performed on a low-hydrocarbon air sample with a manufacturer-specified total hydrocarbon concentration of <1 µmol/mol at room temperature (20° C.) and moderately low pressure (13 kPa). The use of an additional isolator between the mode-matching lenses and a more significant tilt on our detector reduced the influence of the observed etalons.

The relatively low cost instrument described herein is well suited for precise measurements of ultra-trace gas species including radiocarbon and atmospherically relevant free radicals. This instrument has been used to measure birefringence in supermirror coatings and can be applied in addressing other challenges in fundamental physics including the search for symmetrization postulate violations in molecular physics and measurements of absolute number densities for magnetically-trapped ultra-cold molecules using absorption-based techniques.

Example 3. Optical Radiocarbon Detection ($^{14}C$) Using a Quantum Cascade Laser A linear absorption spectrometer that included a cavity ring-down spectrometer with a quantum cascade laser was constructed for optical detection of radiocarbon in the mid-infrared spectral region. The linear absorption spectrometer had a distributed-feedback quantum cascade laser to provide single frequency mid-infrared radiation to probe the $^{14}CO_2$ $v_3$ fundamental transition near 4.5 μm. We achieved a noise-equivalent absorption coefficient of $2 \times 10^{-11}$ $cm^{-1}$ $Hz^{-1/2}$.

Figure 18:
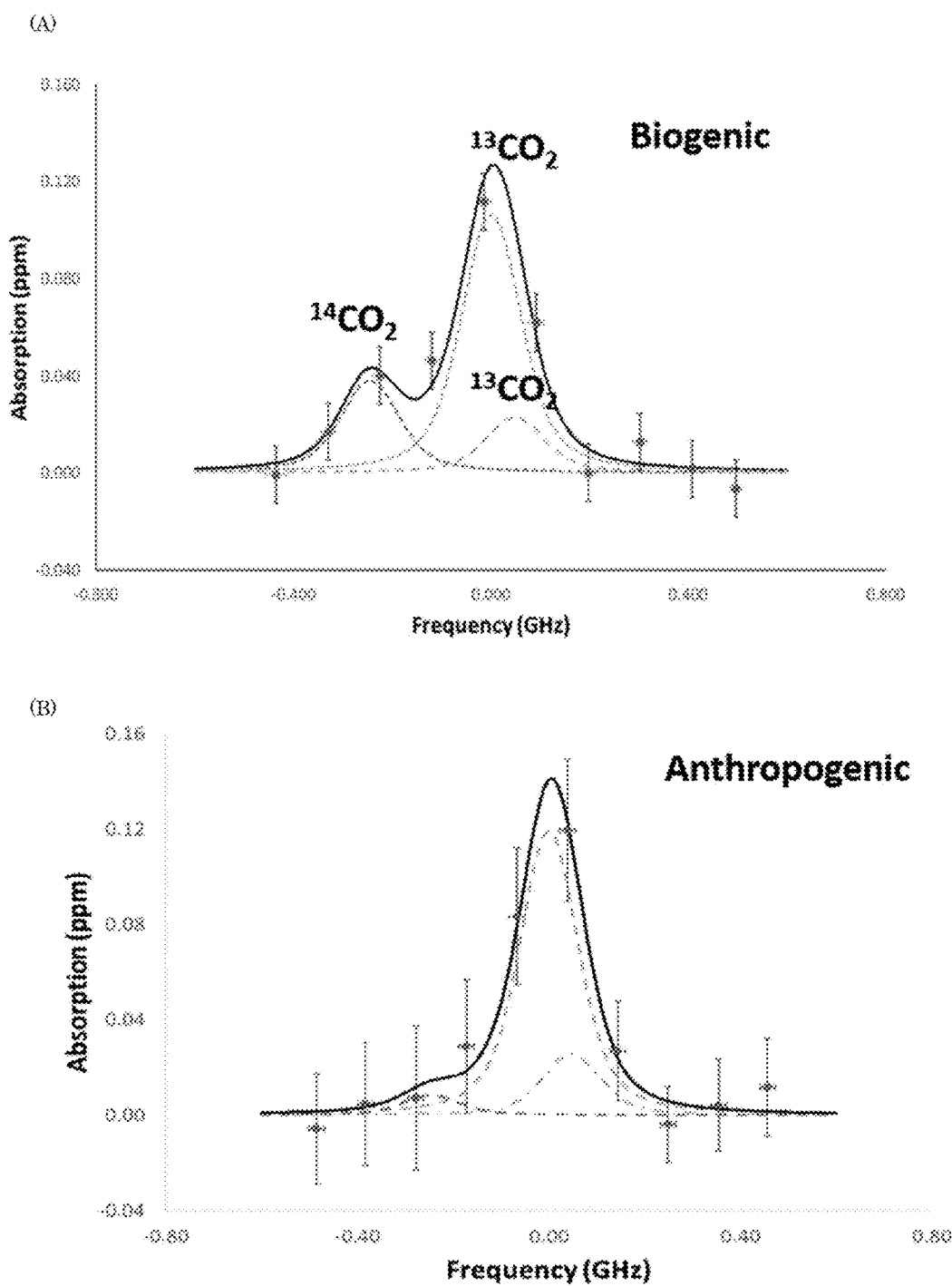
FIG. 18 shows, according to Example 3, an absorption spectrum in panel A of a biogenic CO$_2$ sample. The points show the average (and corresponding standard uncertainties) of 89 spectra. The solid black curve is the average of spectral fits performed on the individual spectra with the dashed curves showing the average of the fits for the component transitions. Panel B shows an absorption spectrum of an anthropogenic CO$_2$ sample, which included 88 spectra.

The linear absorption spectrometer included a low temperature absorption cell with a closed cycle refrigeration system to cool the cell down to 208 K, reducing the interferences from other isotopologues of $CO_2$. The instrument was fully automated and ran unattended for up to 8 h. We made a series of measurements of anthropogenic and biogenic carbon dioxide samples and can quantify the relative abundance of $^{14}C$ within them. Data acquired with the linear absorption spectrometer shown in FIG. 18.

Example 4. Precision Interferometric Measurements of Mirror Birefringence in High-Finesse Optical Resonators In this Example, equations are numbered beginning with Equation 1.

High-finesse optical resonators found in ultrasensitive laser spectrometers utilize supermirrors ideally consisting of isotropic high-reflectivity coatings. Strictly speaking, however, the optical coatings are often nonuniformly stressed during the deposition process and therefore possess birefringence. When physically mounted, the cavity mirrors can be additionally stressed in such a way that large optical birefringence is induced. Here we report a direct measurement of optical birefringence in a two-mirror Fabry-Perot cavity with R=99.99% by observing $TEM_{00}$ mode beating during cavity decays. Experiments were performed at a wavelength of 4.53 with precision limited by both quantum and technical noise sources. We report a splitting of $\delta_v$=618(1) Hz, significantly less than the intrinsic cavity line width of $\delta_{cav} \approx 3$ kHz. With a cavity free spectral range of 96.9 MHz, the equivalent fractional change in mirror refractive index due to birefringence is therefore $\Delta_{n/n}$=6.38(1)$\times 10^{-6}$.

By performing CRDS with a high signal-to-noise ratio in the regime where cavity losses were greater than the round-trip phase retardance, we directly measured mirror birefringence via determination of the lowest-order transverse mode ($TEM_{00}$) splitting. A high-finesse optical resonator (F≈31000) constructed using mid-infrared mirrors with observable birefringence resulted in a unique set of net slow and fast axes which supported orthogonal linear polarization states with different resonant optical frequencies. We observed this small difference in optical frequencies as a beating during the cavity decays for specific input photon polarization states in the presence of appropriate polarization analysis. This method of determining the supermirror birefringence by a measurement of the beat frequency from $TEM_{00}$ mode splitting was, in a sense, a form of birefringence interferometry [4]. Our high-precision CRDS approach had high sensitivity for small amounts of birefringence ($10^{-8}$) as well as more than three orders of magnitude of dynamic range. We also present a complementary generalized model for identifying an ideal input polarization state to optimize high precision retrieval of the cavity decay time constant (and therefore cavity losses) even in the presence of significant mirror birefringence.

Our model of supermirror birefringence in a high-finesse optical resonator begins with the projection of an electric field of arbitrary polarization onto an arbitrary set of spatially orthogonal axes 1 and 2:

$$E(t)=E_1(t)\exp[i(\omega_1 t-\varphi_1)]+E_2(t)\exp[i(\omega_2 t \varphi_2)]. \qquad (1)$$

Here, $E_1(t)$ and $E_2(t)$ are time-dependent electric field magnitudes, $\omega_1$ and $\omega_2$ are the optical angular frequencies of each field ($\omega_1$=2πv$_1$ and $\omega_2$=2πv$_2$, respectively), and $\varphi_1$ and $\varphi_2$ are the phases of each optical field. The natural choice for a basis set is the net slow and fast axes of our optical resonator under study, a linear combination of the slow and fast optical axes of each individual mirror with observable birefringence. We aim to measure the cavity decay after projection onto a linear polarization analyzer (PA) orientated at an angle γ relative to the cavity slow axis. The intensity of the decaying optical field incident on a photodetector after the PA is $$I(\gamma,t)=E(\gamma,t)E^*(\gamma,t)=a_1 f_1 I_1(t)\cos^2(\gamma)+a_2 f_2 I_2(t)\sin^2(\gamma)+\sqrt{a_1 f_1 I_1(t) a_2 f_2 I_2(t)}\sin(2\gamma)\cos(\omega_b t-\delta_\varphi), \qquad (2)$$

where $a_1$ and $a_2$ are the fraction of light intensity propagating along the slow or fast axes (where $a_1+a_2$=1), $f_1$ and $f_2$ are frequency-dependent mode coupling factors (where $f_1+f_2$=1), $I_m(t)=I_0 \exp(-t/\tau_m)$ for m=1 and 2, and $\omega_b$ and $\delta_\varphi$ are the difference in angular frequency and phase between the slow and fast electric fields, respectively. In the limit where the laser line width is much greater than both the cavity line width and the birefringence splitting (i.e., $\Delta v_{laser}$ $\delta_{cav}$ and $\gg \omega_b/(2\pi)$) on the timescale of cavity buildup, the frequency-dependent mode coupling factors become identical and constant.

If in addition we consider the mirror reflectivity to be the same for both axes (i.e., $\tau_1=\tau_2 \equiv \tau$), Eq. (2) simplifies to Eq. (3):

$$\frac{I(\gamma,t)}{I_0}=\exp(-t/\tau)[A(\gamma)+B(\gamma)\cos(\omega_b t-\delta_\varphi)]. \qquad (3)$$

The factors $A(\gamma)$ and $B(\gamma)$ depend upon the polarization state by which the optical resonator is excited. Here we investigate in detail two specific cases: excitation with circularly polarized light and excitation with linearly polarized light. For circular excitation, $a_1=a_2$=1/2 and the absolute difference in phase is $|\delta_\varphi|$=π/2. Thus, $A(\gamma)$=1, $B(\gamma)$=sin(2γ), and $\delta_\varphi=\pm\pi/2$ for left-hand (LH) and right-hand (RH) excitation, respectively. Equation (3) can then be further simplified using the small-angle approximation $\sin(\omega_b t) \approx \omega_b t$:

$$\frac{I(\gamma,t)}{I_0}=\exp[-t(1/\tau \mp B(\gamma)\omega_b)]. \qquad (4)$$

In the limit of weak birefringence and using circular excitation, the cavity decay filtered by a linear PA will be nearly exponential with an effective time constant of $\tau_{eff}(\gamma)=\tau/[1 \mp B(\gamma)\omega_b \tau]$ for LH and RH excitation. The maximum fractional deviation from τ is then defined as eff,max $$\tau \approx \omega_b \tau. \qquad (5)$$

For excitation with linearly polarized light, the following conditions are met: $\eta=\tan^{-1}(\sqrt{a_2/a_1})$ where $\eta$ is the angle the incident linearly polarized field makes with the net slow axis, and $\delta_\varphi=0$. In each of the experiments described here using linearly polarized light, $\eta=\gamma$. Making the substitution, $A(\gamma)=\cos^4(\gamma)+\sin^4(\gamma)$ and $B(\gamma)=\sin^2(2\gamma)/2$, a similar expression to Eq. (4) can then be derived using the small-angle approximation $\cos(\omega_b t)\approx 1-(\omega_b t)^2/2$:

$$\frac{I(\gamma,t)}{I_0} = \exp[-t/\tau - B(\gamma)(\omega_b t)^2/2]. \quad (6)$$

In SI units to $I_0 = pc\epsilon_0 T_c(\langle I_{1,0}\rangle + \langle I_{2,0}\rangle)/2$, where the coefficient $p=1/4$ or $p=1/2$ for circular or linear excitation, respectively, is the permittivity of free space, $T_c$ is the overall efficiency with which the incident spectrum is transmitted by the optical resonator, and denotes an averaging over optical cycles. Since our cavity design does not allow for one mirror to be rotated in a systematic fashion relative to the other, we must describe the two-mirror optical resonator and thus only model net cavity birefringence.

The above expressions provide an intuitive, parameterized description of a single-mode cavity decay with $TEM_{00}$ mode beating that arises from the presence of mirror birefringence. As evidenced by the experiments reported here, the general time-domain approach quantitatively described cavity excitation by both circularly and linearly polarized light without ignoring polarization-dependent loss. We also introduce frequency-dependent mode coupling factors that, for the case of a swept laser-cavity locking scheme, renders these analytical expressions useful for cases of both weak and strong birefringence (relative to the round-trip cavity losses).

A cavity round-trip Jones matrix M contains the following parameters: the round-trip phase retardance $\in=\omega_b t_r/2$ and the angle $\alpha$ the slow axis makes with the x axis in the laboratory frame. We can now make a connection between the perturbed exponential expressions derived above from an intuitive description of transverse mode beating and the Jones matrix approach. Through Eq. (5) $\Delta\tau/\tau=\in/(1-R)$ and the above definition of round-trip phase retardance, we find for excitation of the cavity by circular polarization that in the limit of weak birefringence. In its general form, M also treats polarization-dependent loss in each cavity mirror, a small perturbation on supermirror birefringence that has not been included in Eqs. (3)-(6).

Figure 19:
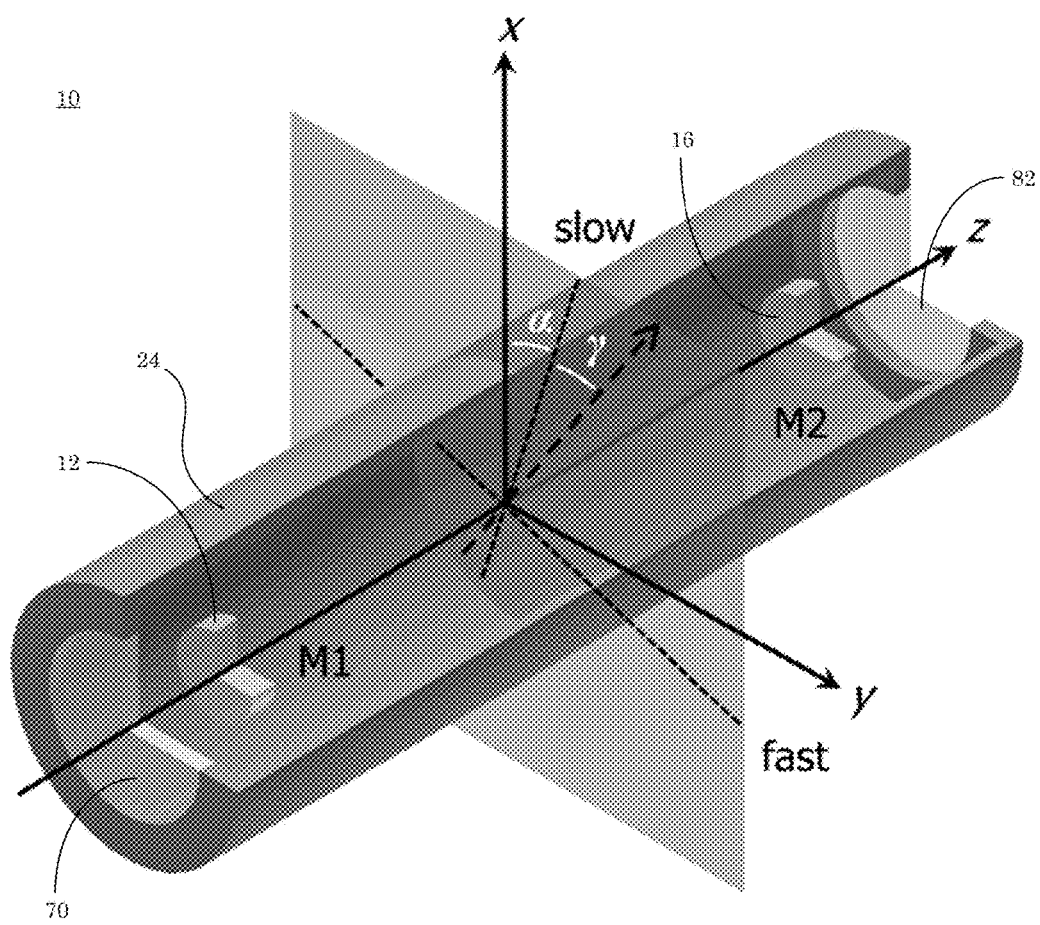
FIG. 19 shows, according to Example 4, an exemplary high-finesse optical resonator. Supermirrors are labeled M1 and M2. CaF$_2$ windows with antireflective coating isolated the optical resonator from the laboratory. Net slow and fast optical axes are illustrated using dashed lines, and the linear polarization analyzer (PA) orientation using a dashed arrow. The angle between the slow axis and the x axis is defined as $\alpha$, whereas the angle between the slow axis and the PA is defined as $\gamma$. When studying the cavity response to linear excitation, the angle $\eta$ that the incident linearly polarized light makes with the slow axis (not shown) is equal to $\gamma$.

A schematic of the linear absorption spectrometer that performed ultrasensitive cavity ring-down spectroscopy (CRDS) in the mid-infrared spectral region is shown in FIG. 19. The optical resonator was excited by a continuous-wave distributed feedback quantum cascade laser (QCL) operating at 4.53 µm and with an average output power of ≈30 mW. The polarization state of the QCL output is linear. A germanium acousto-optic modulator (AOM) was used as a fast optical switch to initiate cavity decays while a low-bandwidth (≈4 Hz) transmission lock maintained resonance between the single-frequency QCL and a given mode of the optical resonator by feeding back to the laser current. A low noise liquid-$N_2$-cooled InSb photodetector of 100 µm diameter with trans impedance gain of $1\times10^6$ V/A, responsivity of 3.7 A/W, and a 1 MHz bandwidth was used to record individual cavity decay events with a measured noise-equivalent power of 70 fW $Hz^{-1/2}$. The decays were digitized with 22-bit resolution at a sampling rate of 1 MS/s and a 3 dB electronic bandwidth of 480 kHz.

The high-finesse optical resonator under interrogation included two supermirrors from the same batch coated for maximum power reflectivity R at a wavelength of 4.6 µm (CRD Optics 901-0008-4600). The supermirrors were created using ZnSe substrates of the following dimensions: a thickness of 5 mm, a diameter of 2 cm, and a radius of curvature of 1 m. The mirrors were glued to 2.54 cm outer diameter (OD) adapter rings using standard two-part epoxy and then mounted inside a threaded stainless steel knife-edge flange using a single aluminum retaining ring. Each of the two mirror mounts was adjusted using high-thread-count set screws to aid in initial alignment of the optical resonator. The optical resonator length was L=1.55 m, and the round-trip absorption and scattering losses were measured to be $1\times10^{-4}$.

The individual zero-pressure difference mirror mounts were supported by stainless steel brackets, each of which was connected to the other by four spacer members (2.54 cm OD Invar-36 rods). The supermirror zero-pressure difference mirror mounts were connected by a stainless steel tube of 1.27 cm OD and a stainless steel bellows to reduce strain in the event of slow drifts in cavity length due to room temperature fluctuations. This tube housed the optical mode as well as any sample gas under study. Each mirror mount was capped with a $CaF_2$ window with antireflective coatings which sealed the entire optical resonator from the laboratory environment. The mirrors in this design experience a zero-pressure difference between their antireflective and reflective faces, significantly reducing the potential for stress-induced birefringence. Experiments were performed under the vacuum of a turbomolecular pump at pressures<1.3 Pa.

Figure 20:
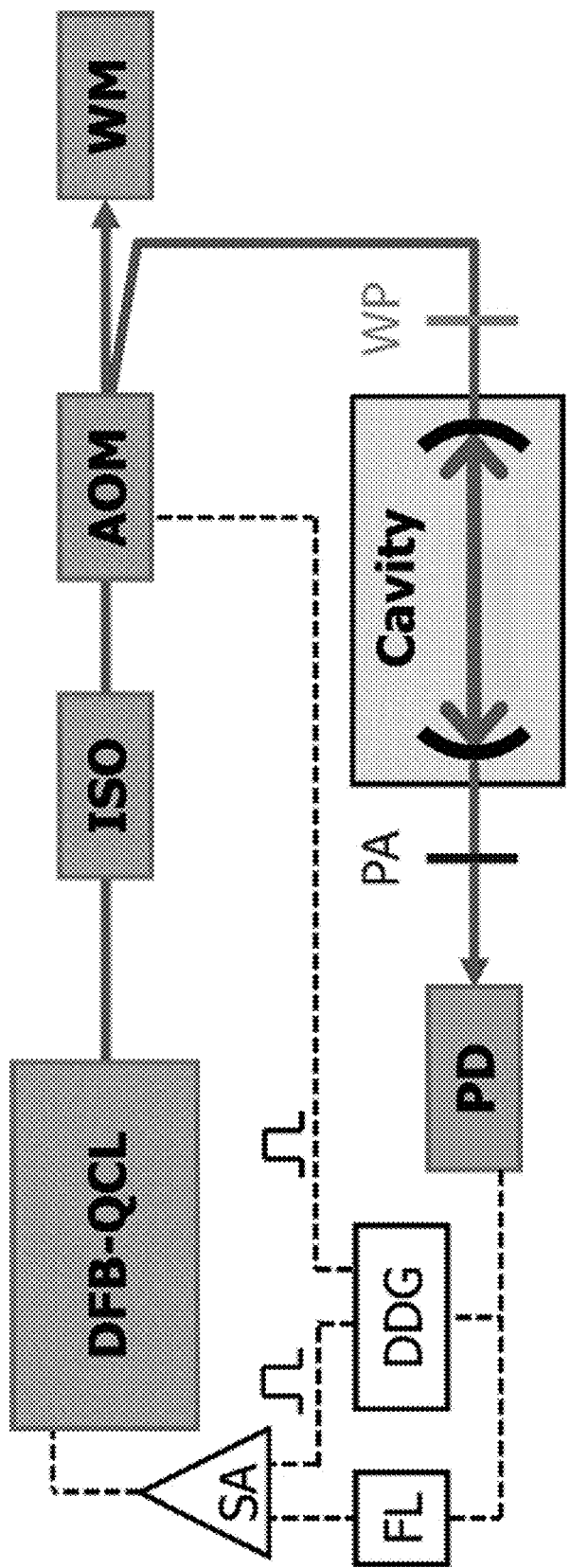
FIG. 20 shows, according to Example 4, a diagram of the cavity ring-down spectrometer. The optical components (dark gray boxes) are DFB-QCL, distributed feedback quantum cascade laser; ISO, optical isolator; AOM, acousto-optic modulator; WM, wavelength meter; and PD, photodetector. Also shown are a wave plate (WP, orange) and linear polarization analyzer (PA, blue). Electronic components (white boxes) are DDG, digital delay generator; FL, feedback loop; and SA, summing amplifier. Free-space laser propagation is shown as solid red lines, whereas electronic cables are shown as black dashed lines. TTL signals for optical switching are illustrated where appropriate.

Results of exciting the two-mirror optical resonator with circularly polarized light are presented. A quarter-wave plate (Altechna 2-IRPW-L/4-4500-C) and a high-contrast PA (ISPOpticsPOL-1.5-5-SI,extinction 10000:1) were arranged at positions WP and PA as shown in FIG. 20. For each of two orientations of the quarter-wave plate (LH and RH circular), we recorded cavity decay events at various linear projection angles $\theta=\alpha+\gamma$ provided by the PA. Decay signals were recorded at a constant trigger threshold of 150 mV, which allowed for a 3 s total acquisition time at rates that ranged from 2 to 14 Hz.

Figure 21:
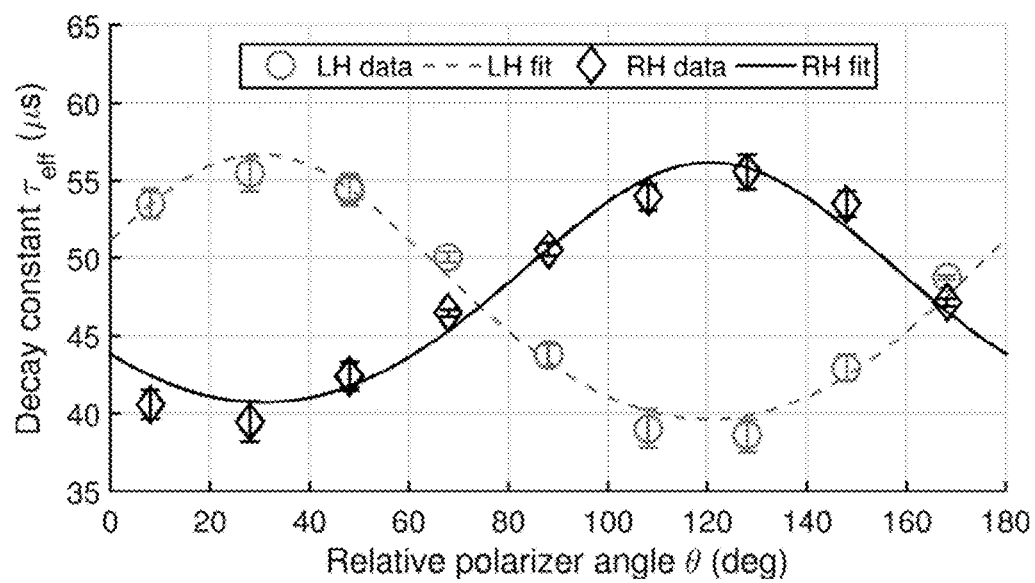
FIG. 21 shows, according to Example 4, an effective cavity decay time constant $\tau_{eff}$ as a function of $\theta$, the angle provided by the PA relative to the laboratory x axis. Also shown are expanded uncertainties (±3$\sigma$) for each 3 s acquisition. Repeated measurements are plotted at $\theta$=48° for each LH and RH data set to illustrate $\theta$ modulo 180° reproducibility.

At each angle $\theta$ the average empty-cavity decay constant $\tau_{eff}$ for a 3 s acquisition ensemble is shown in FIG. 21 for both LH (blue circles) and RH (black diamonds) circularly polarized excitation. A constant offset was subtracted from each individual cavity decay, which was then fit to a single exponential decay constant, $\tau_{eff}$, and a floated amplitude using a nonlinear-least-squares Levenberg-Marquardt algorithm.

For each respective handedness, the LH and RH data sets were fit to the model $\tau_{eff}(\theta)=\tau[(1\mp\omega_b\tau\sin[2(\theta-\alpha)])]^{-1}$, where $\omega_b=2\pi\delta_v$. The fit parameters from FIG. 21 were $\tau=46.7(4)$ µs, $\delta_v=600(40)$ Hz, and $\alpha=-14.9(1.7)°$ for the LH data set and $\tau=47.2(4)$ µs, $\delta_v=540(40)$ Hz, and $\alpha=-14(2)°$ for the RH data set, respectively. From the weighted average of the model parameters retrieved from each data set we determined $\tau=46.9(3)$ µs, $\delta_v=570(30)$ Hz, and $\alpha=14.7(1.5)°$.

Of the fit $\tau_{eff}$ in FIG. 21, the LH excitation data point at $\theta=168°$ exhibited the smallest relative standard deviation of $\sigma_\tau=0.044$ µs. This led to minimum observed fit statistics of $\sigma_\tau/\tau=0.09\%$, about a factor of three from the theoretical value of $\sigma_\tau/\tau=0.027\%$ (the quadrature sum of the quantum noise $\sigma_\tau/\tau=0.011\%$ and the detector noise $\sigma_\tau/\tau=0.025\%$, respectively) calculated when $I^-_0=81(10)$ nW of light was incident on the photodetector ($I^-_0$ was the average of all data reported in FIG. 21, with ±1a standard deviation in parentheses). All decays were fit beginning 20 μs after the AOM optical switch to avoid occurrences of spurious optical pumping of the cavity as well as to reduce the influence of higher order transverse modes.

Figure 22:
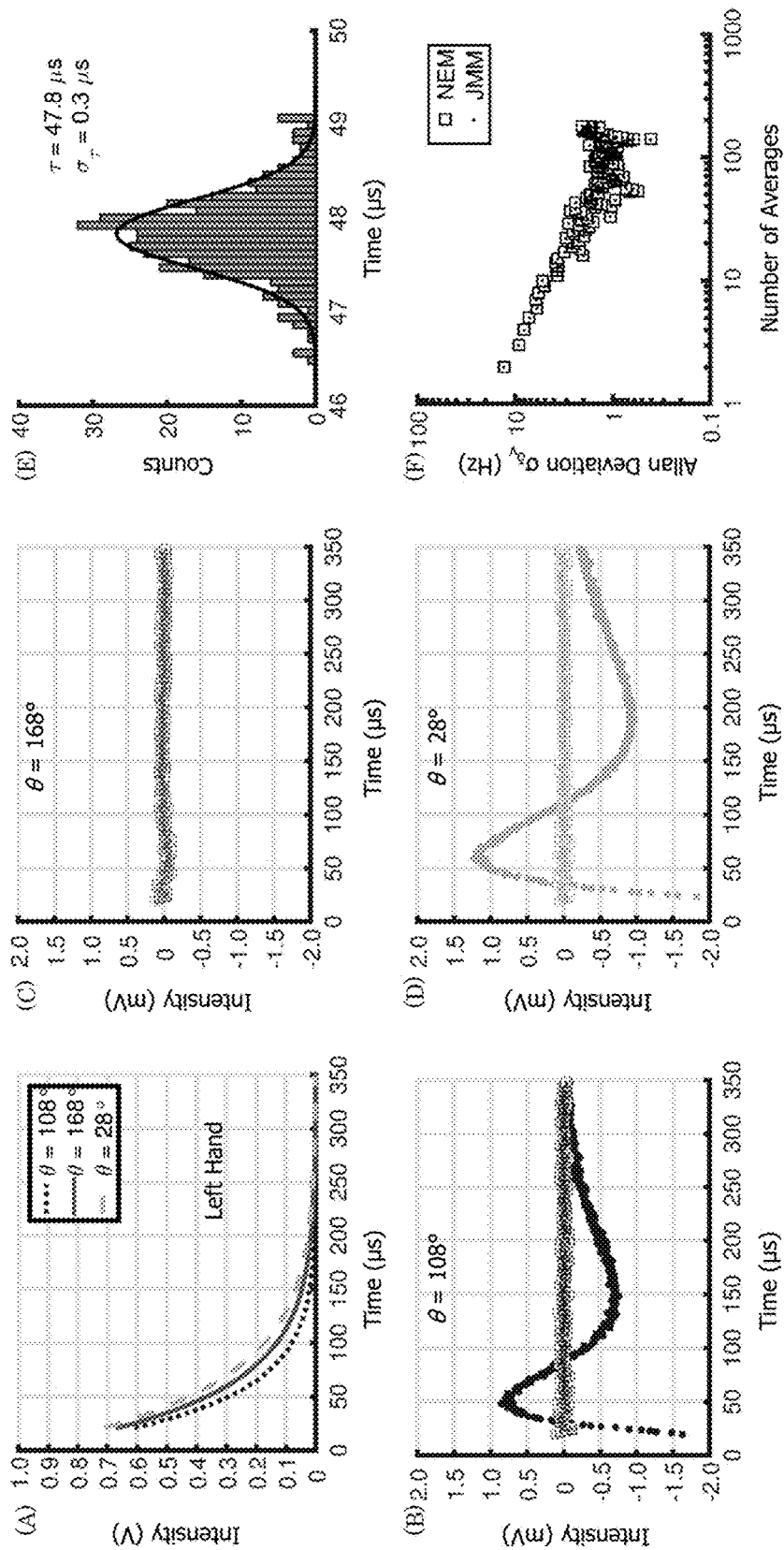
FIG. 22 shows, according to Example 4, (panel A) cavity decays at various angles $\theta$ for LH excitation. (Panels bd) Fit residuals from the single exponential model (SEM, solid circles), the nonexponential model (NEM, open squares), and the Jones matrix model (JMM, small dots). The NEM and JMM residuals are identical for all $\theta$. (Panel E) Histogram of the fitted $\tau$ from the JMM for 346 unique cavity decays recorded at five different values of $\theta$ for LH and RH excitation separated into 35 bins. A fitted normal distribution is shown as a solid black line. The histogram of fitted $\tau$ values using the NEM is identical (not shown). (Panel F) Allan deviation of fitted $\delta v$ for linear excitation at $\theta$=33° recorded at an acquisition rate of 9 Hz.

The observed cavity decays when $\sigma_\tau$ is at its extrema is presented here. FIG. 22 shows the measured cavity decays along with the corresponding fit residuals arising from three decay models: the single-exponential model (SEM) using $\tau_{\mathit{eff}}$, the nonexponential model (NEM) of Eq. (3), and a Jones matrix model (JMM) in the limit of no polarization-dependent loss (PDL). For LH excitation, exponential decays at three distinct values of θ are plotted in panel A of FIG. 22. Each of these decays were fitted by the SEM [solid circles in panels B–D of FIG. 22], the NEM (open squares), and the JMM (small dots). For the NEM and JMM, α=−14.7° was held constant at all θ and an amplitude parameter, τ, and $\delta_v$ were all floated during the fit. When |sin [2(θ−α)]| was at a maximum the SEM left large residuals, whereas the SEM did well when |sin [2(θ−α)]|≈0 at θ≈168°. In panel C of FIG. 22, the solid circles of the SEM, effectively identical to the NEM and JMM, are obscured from view. While the SEM failed to model the cavity decays at all θ, the NEM and JMM are indistinguishable from one another and performed well over all θ. A similar pattern was observed for RH excitation (not shown).

At each value of θ, the NEM and JMM provided fitted values for the amplitude of the decay, a single global time constant τ and the beat frequency $\delta_v$. Panel E of FIG. 22 shows the ensemble of fitted τ values acquired at all θ where a beat was observed. The τ values are well approximated by a normal distribution with τ=47.8 μs and $\sigma_\tau$=0.3 μs (identical for both the NEM and JMM). For the same decays, the ensemble of fitted values of $\delta_v$=600 Hz exhibits a larger relative standard deviation of $\sigma_{\delta v}$=60 Hz. For the two angles of θ measured in the laboratory with the largest perturbation from birefringence (θ=28° and 128°, respectively) and therefore the largest signal-to-noise ratio on the beat, we measure $\delta_v$=610 Hz and $\sigma_{\delta v}$=30 Hz. At θ=28° following LH circular excitation the perturbation from birefringence is near maximum, since θ≈α. At an acquisition rate of 9 Hz, we report a measurement precision of $\sigma_{\delta v}$=6 Hz in 1 s of averaging on a measured value of $\delta_v$=613 Hz.

Excitation of the cavity by linear polarization can also be treated by both the NEM and JMM using the appropriate coefficients A(γ) and B(γ) in Eq. (3). When η=γ, rotating η and γ together is equivalent to rotating the cavity itself relative to a fixed linear polarization. We note that, at a constant trigger threshold, this approach does not suffer from any potential bias due to changes in the intracavity power as a function of the angle of the linear polarization analyzer. Exciting the cavity at θ=33° (near where τ/τ for circular polarization in FIG. 21 was largest) results in decays with the largest deviation from the SEM. The measured beat frequency at θ=33° is $\delta_v$=618 Hz with an improved precision of $\sigma_{\delta v}$=1 Hz due to a the longer 19 s acquisition time [see panel F of FIG. 22]. With a cavity-free spectral range of FSR=96.9 MHz, this equates to a measured fractional change in refractive index of $\Delta n/n = \delta_v/\mathrm{FSR} = 6.38(1) \times 10^{-6}$. Precision on the $10^{-8}$ level is one order of magnitude better than for a cavity of F≈420000 at a wavelength of 800 nm.

The Allan deviation for the linear excitation measurement shown in panel F of FIG. 22 demonstrated that averaging times>10 s were possible. The agreement between the reported values of $\delta_v$ for both circular and linear excitation given their respective values of $\sigma_{\delta v}$ is excellent when considering that these data sets were recorded several days apart. This suggests that long-term drift in the net cavity birefringence due to temperature changes in the laboratory are no more significant than our current short term measurement precision.

In CRDS, we desire to simply avoid mirror birefringence altogether to achieve optimized fit statistics for the unperturbed cavity time constant τ. With knowledge of the spatial location of the slow and fast cavity axes in the laboratory frame we can selectively excite one of the modes and measure the Allan deviation to determine an NEA normalized to a 1 s acquisition. When θ=168° (η=γ≈3°, I₀=203 nW) we report $\sigma_\tau/\tau$=0.024% for the SEM, within a factor of two of the theoretical value of $\sigma_\tau/\tau$=0.012% calculated from the quadrature sum of quantum and technical noise when the fitting is performed with appropriate weighting. This results in an NEA=$5.5 \times 10^{-11}$ cm$^{-1}$ Hz$^{-1/2}$ at an acquisition rate of only 9 Hz. If in the laboratory the exact condition θ=α (or θ=α±90°) is met with excitation by linear polarization, we can indeed achieve the theoretical limit of $\sigma_\tau/\tau$ set by both quantum and detector noise.

When (and therefore $\delta_v < \delta_{cav}$) both the NEM and JMM perform equally well in the limit where PDL is negligible (and at the experimental signal-to-noise ratio on the cavity decays of SNR 3000:1). To measure the PDL we have fit the average cavity decays at each value of θ for the LH and RH data sets to a global set of parameters that includes PDL in the JMM. Each averaged cavity decay was normalized by its previously fit amplitude and then collectively fit using the JMM+PDL with the following floated terms: τ, α, ∈, b, and β, where $b = (r_{max} - r_{min})/(r_{max} + r_{min})$ (r is the net field reflectivity of the mirrors) and β is the angle $r_{max}$ makes with the x axis. We report b/∈=0.057(16) with β=17(12)° and b/∈=0.09(7) with β=60(20)° for the LH and RH data sets, respectively. Clearly PDL is a small perturbation on the mirror birefringence, and we can safely place an upper bound of b/∈<0.1 on the net cavity PDL for this pair of mirrors.

The simultaneous fit over all θ within a data set returns large uncertainties in β, again suggesting that PDL is small. A TEM₀₀ mode splitting approaches the cavity line width $\delta_v \approx \delta_{cav}$), involving frequency-∈≈1−R dependent mode coupling factors $f_1$ and $f_2$ in the NEM when a ∈≈1−R narrow line width continuous-wave laser is coupled to the optical resonator. In this strong birefringence regime ($\delta_v \geq \delta_{cav}$), $f_1$ and $f_2$ will change for every cavity decay recorded by our spectrometer due to the swept laser locking and thresholding used to trigger the optical switch. The small-angle approximations used to derive Eqs. (4)-(6) are not justified when, and the SEM fails even more dramatically than shown in FIG. 22. The use of Eq. (5) to estimate $\omega_b$ from the SEM of decays following LH and RH excitation is no longer valid, and the full NEM or JMM must be applied. When $\delta_v \approx \delta_{cav}$, $1/\omega_b \approx \tau$. Making the substitution into Eq. (5), we see that $\Delta\tau/\tau \approx 1$ and cavity decays are expected to be far from exponential.

By replacing M1 of the optical resonator with a presumably identical supermirror we fortuitously observed strong net birefringence in the regime. For LH, RH, and linear excitation we identified several PA orientations in the laboratory frame where the SEM produced large fitted residuals. For 133 total cavity decays fitted by Eq. (2) (still under the assumption of no PDL, i.e., $\tau_1 = \tau_2 = \tau$) at various θ we report $\delta_v$=3.1 kHz with a standard deviation of 0.4 kHz. We observed a maximum deviation from the SEM for LH excitation at θ=138° (i.e., α=93°) and proceeded to record 170 successive cavity decays at an acquisition rate of 17 Hz with the PA in that orientation. The average beat frequency for the θ=138° data set was $\delta_v$=2.789 kHz with 9 Hz precision at 5 s of averaging. An Allan plot revealed that the √ deviation of $\delta_\nu$ remained inversely proportional to the N, where N is the number of cavity decays, for a minimum of 5 s. Therefore, with longer averaging times it may be possible to again achieve 1 Hz precision even in the presence of strong mirror birefringence.

The origin of the observed strong mirror birefringence that coincided with replacing a single mirror of the optical resonator could be reasoned in one of two ways. Since we measured net birefringence, the new M1 could simply have significantly larger birefringence than the first M1. Alternatively, the relative orientations of $\alpha_{M1}$ and $\alpha_{M2}$ could be very different in the two optical resonators, meaning that in our first optical resonator with $\delta_\nu$=618 Hz the slow and fast axes of the individual supermirrors were oriented close to 90° from one another in the laboratory frame.

Example 5. High-Precision Measurements of Mid-Infrared Supermirror Birefringence Mid-infrared supermirror birefringence using cavity ring-down spectroscopy was determined. Analysis of the beating observed during cavity decays yielded a $\Delta n/n$ sensitivity on the order of $10^{-8}$ at a wavelength of 4.5 µm.

In an optical cavity, after every round-trip, photons leak from the cavity by a fractional amount equal to the sum of the mirror transmission T and losses L (the total of mirror absorption and scattering as well as intracavity losses). Remaining photons are reflected at the mirror surface. Therefore, the fate of any photon following one resonator round trip can be described by the expression R+T+L=1, where R is the power reflection coefficient. The rate at which photons leak from an optical resonator is $\tau$=l/[c(1−R)], where l is the resonator length. By precisely measuring $\tau$, detailed information regarding the total intracavity losses T+L is learned. In cavity ring-down spectroscopy (CRDS), the precision measurement of $\tau$ as a function frequency allows for the molecular spectroscopy of trace gases to be performed with ultrahigh sensitivity.

Determined here were perturbations to empty cavity $\tau$, $\tau_0$, that arise from ultralow supermirror birefringence. We excited the mid-infrared optical resonator (to be used for CRDS) with either a circularly or a linearly polarized continuous-wave (CW) laser and thus identified the spatial location of each birefringence cavity eigenmode. This resulted in a measurement of the relative difference in their refractive index, $\Delta n/n$, with $10^{-8}$ precision. Identifying the polarization conditions that resulted in the highest precision retrievals of $\tau$ provided optical detection of radiocarbon dioxide, $^{14}CO_2$, below its nature abundance of 1.2 parts-per-trillion (ppt).

Figure 23:
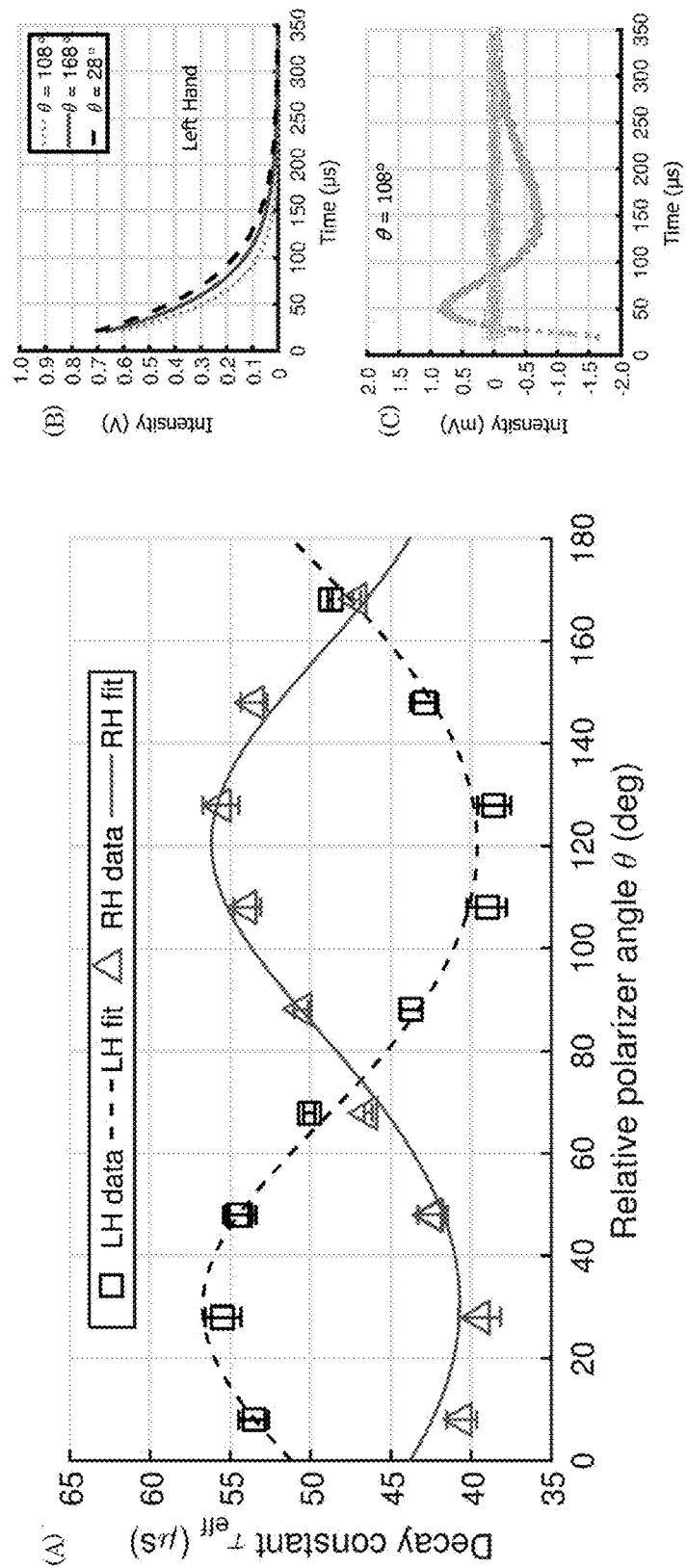
FIG. 23 shows, according to Example 5, (panel A) an effective cavity decay constant vs. polarizer angle. Panel B shows example CRDS signals. Panel C shows residuals when fitting with a single exponential (large blue circles) model or the models that included supermirror birefringence (small dots and open squares)

Panel A of FIG. 23 shows the effective empty cavity decay constant $\tau_{eff}$ vs. the angle of a linear polarization analyzer located after the optical resonator but before the CRDS photodetector. The cavity was excited by either left-handed (LH, red squares) or right-handed (RH, gray triangles) circularly polarized light. Large deviations in $\tau_{eff}$ are observed, but a sinusoidal pattern is clear. Panel B of FIG. 23 shows cavity decays. A closer examination of the CRDS fit residuals (blue circles in panel C of FIG. 23) revealed large oscillations at the extrema of panel A of FIG. 23. These oscillations are a result of beating between the split resonator modes due to the presence of non-negligible supermirror birefringence.

Panel C of FIG. 23 shows residuals that result from modeling the supermirror birefringence. Using both an analytical expression (small dots) for cavity mode beating as well as a Jones matrix model (open squares), it was possible to fit the CRDS signals in the presence of supermirror birefringence. A maximum fraction deviation from $\tau_0$ in the limit of small birefringence and circularly polarized excitation can be approximated.

Figure 24:
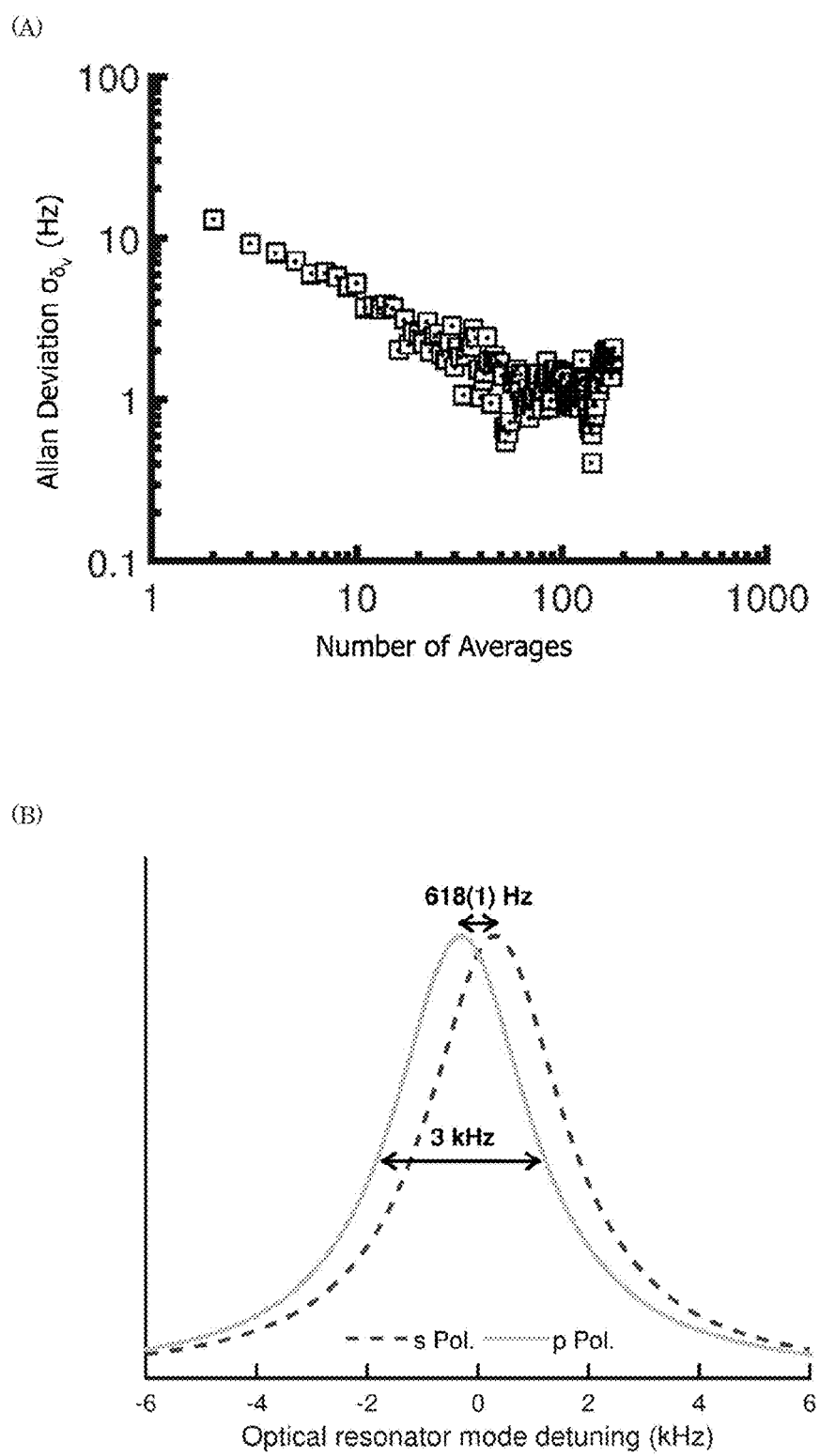
FIG. 24 shows, according to Example 5, (panel A) Allan variance of measured birefringence splitting under linearly polarized excitation conditions. Panel B shows a frequency-domain picture of the birefringence mode splitting.

By including mode beating in or model of the CRDS signals, we extracted a high-precision measurement of $\delta_\nu$. Panel A of FIG. 24 shows an Allan plot of the standard deviation in the birefringence splitting vs. the number of CRDS signals following linear excitation of the cavity at $\theta$=33°. At a modest integration time of only 11 s (100 CRDS signals at an acquisition rate of 9 Hz), we report a birefringence splitting of 618 Hz with an uncertainty of 1 Hz. With a cavity free spectral range of 97 MHz, the fractional change in mirror refractive index due to birefringence is therefore $\Delta n/n$=6.38(1)×$10^{-6}$. The frequency-domain picture of the measured birefringence mode splitting is shown in panel B of panel A of FIG. 24.

The data represent direct measurement of supermirror birefringence by birefringence interferometry, i.e., the time-domain measurement of optical mode beating in the CRDS signals.

Figure 25:
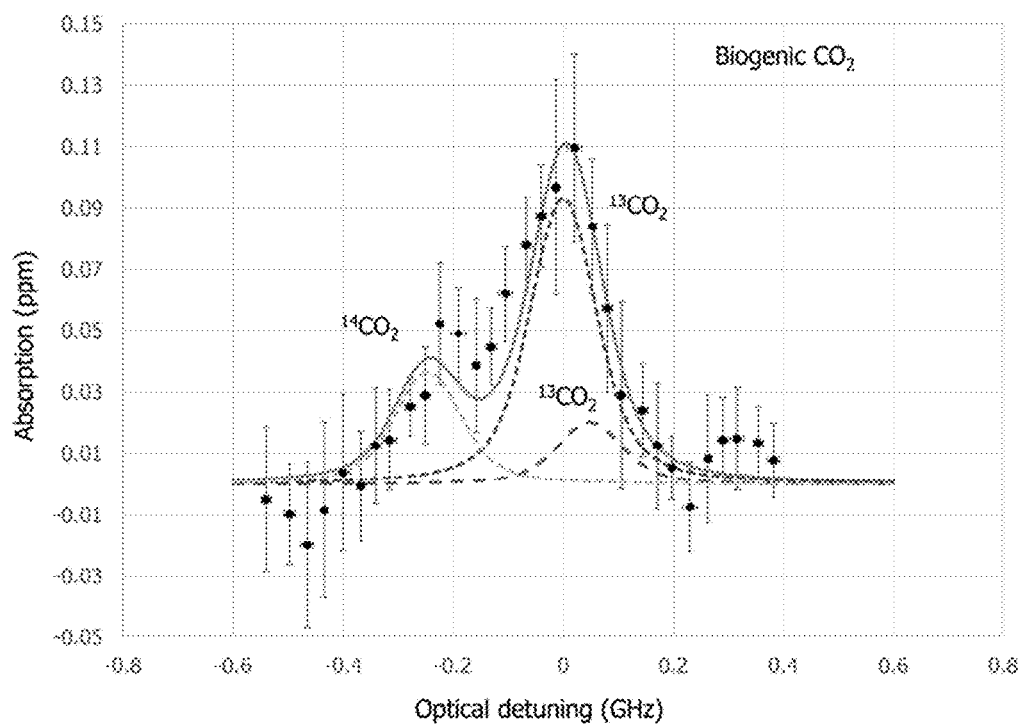
FIG. 25 shows, according to Example 5, an absorption spectrum of biogenic CO$_2$ sample. Experimental data with error bars are shown as points, and the total fit molecular spectrum is shown as a solid line.

Cavity-enhanced mid-infrared spectroscopy provided by the linear absorption spectrometer provided trace detection of rare $CO_2$ isotopologues, specifically, radiocarbon dioxide ($^{14}CO_2$) at a wavelength of 4.5 µm. Radiocarbon dioxide can be used to clearly differentiation) between $CO_2$ that originated from either biogenic or anthropogenic sources. Here, we report the all optical, quantitative detection of $^{14}CO_2$ using a QCL and CRDS as shown in FIG. 25, that substantially reduced the instrument cost and simplified signal analysis over conventional instruments and methods. The ultimate sensitivity of the linear absorption spectrometer here was noise-equivalent absorption coefficient of NEA=2.6×$10^{-11}$ $cm^{-1}$ $Hz^{-1/2}$.

For the experiments in this Example, a linearly polarized CW quantum cascade laser (QCL) operated at a wavelength of 4.5 µm to excite one longitudinal $TEM_{00}$ mode of a high finesse optical resonator including a two-mirror Fabry-Perot optical resonator. Wave plates, either $\lambda/4$ or $\lambda/2$, were used to control the laser polarization prior to the optical resonator, and a linear polarization analyzer was used after the cavity but before the photodetector to identify the spatial location of each linear birefringence eigenmode. An acousto-optic modulator was used as a fast optical switch to initiate CRDS signals. Laser-cavity coupling was maintained by a loose, low-bandwidth (4 Hz) transmission lock.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A linear absorption spectrometer to optically determine an absolute mole fraction of radiocarbon in a sample, the linear absorption spectrometer comprising:
    a laser light source that provides mid-infrared laser light for linear absorption by the radiocarbon in the sample;
    a high finesse optical resonator that is actively stabilized in a resonance frequency and comprising:
    a first supermirror comprising a first radius of curvature that provides cavity ring down reflection and that receives the mid-infrared laser light;
    a second supermirror comprising a second radius of curvature that provides cavity ring down reflection, the second supermirror in combination with the first supermirror comprises a relative difference of refractive index $\Delta n/n$ from $1\times10^{-8}$ to $6\times10^{-6}$, such that the second supermirror transmits cavity ring down light from communicating the mid-infrared laser light through the sample in a sample cell;
    the sample cell interposed between the first supermirror and the second supermirror to contain the sample, the sample cell operating at a temperature from 220 K to 300 K during linear absorption of the mid-infrared laser light by the radiocarbon and comprising:
    a linear absorption optical path length that is greater than a kilometer (km);
    a first zero-pressure difference mirror mount on which the first supermirror is disposed and mechanically coupled to the sample cell;
    a second zero-pressure difference mirror mount on which the second supermirror is disposed and mechanically coupled to the sample cell;
    an optical switch interposed between the laser light source and the high finesse optical resonator such that the optical switch receives the mid-infrared laser light from the laser light source, modulates the mid-infrared laser light, and communicates modulated mid-infrared laser light to the first supermirror of the high finesse optical resonator;
    a photoreceiver in optical communication with the high finesse optical resonator and that receives the cavity ring down light from the second supermirror, the photoreceiver comprising a noise equivalent power that is less than a shot noise limit of the cavity ring down light,
    the linear absorption spectrometer providing the absolute mole fraction of the radiocarbon in the sample for the absolute mole fraction being from 1 part-per-quadrillion to 2.5 parts-per-trillion of radiocarbon in the sample.

2. The linear absorption spectrometer of claim 1, wherein the sample comprises a gas.

3. The linear absorption spectrometer of claim 2, wherein the gas is from a petrogenic source or from a biogenic source.

4. The linear absorption spectrometer of claim 1, wherein the laser light source comprises a semiconductor laser.

5. The linear absorption spectrometer of claim 4, wherein the semiconductor laser comprises a quantum cascade laser.

6. The linear absorption spectrometer of claim 1, wherein the mid-infrared laser light in the high finesse optical resonator comprises a fractional frequency stability that is greater than 1 in $10^8$.

7. The linear absorption spectrometer of claim 1, wherein the mid-infrared laser light comprises a mid-infrared optical comb,
    the mid-infrared optical comb comprises a fractional frequency stability that is greater than 1 in $10^{11}$.

8. The linear absorption spectrometer of claim 7, wherein the mid-infrared optical comb comprises a wavelength from 2 micrometers (μm) to 20 μm.

9. The linear absorption spectrometer of claim 1, wherein the linear absorption optical path length comprises a length from 1 km to 600 km.

10. The linear absorption spectrometer of claim 1, wherein a reflectivity of the first supermirror and the second supermirror independently is from 99.9% to 99.99999% at a wavelength of the mid-infrared laser light.

11. The linear absorption spectrometer of claim 1, further comprising a reference laser,
    wherein a reflectivity of the first supermirror and the second supermirror independently is from 50% to 99.7% at a wavelength of the reference laser light.

12. The linear absorption spectrometer of claim 1, further comprising a reference laser,
    wherein the reference laser is a second quantum cascade laser stabilized to an optical frequency comb.

13. The linear absorption spectrometer of claim 1, a pressure in the sample cell in a presence of the sample is from 100 Pascals to 3 kilopascals.

14. The linear absorption spectrometer of claim 1, wherein the sample cell further comprises:
    a primary fluid conduit disposed from the first supermirror to the second supermirror and that receives the sample such that the sample is disposed in the primary fluid conduit during linear absorption by the sample; and a secondary fluid conduit disposed in the primary fluid conduit and that receives a cooling fluid such that the secondary fluid conduit cools the sample cell to the temperature from 220K to 300K.

15. The linear absorption spectrometer of claim 14, wherein the secondary fluid conduit is isolated from fluid communication with the primary fluid conduit.

16. The linear absorption spectrometer of claim 1, wherein the high finesse optical resonator further comprises a spacer member to space apart the first zero-pressure difference mirror mount and the second zero-pressure difference mirror mount.

17. The linear absorption spectrometer of claim 1, wherein the photoreceiver further comprises a distance from the second supermirror equivalent to an integer multiple of a distance between the second supermirror and the first supermirror.

18. The linear absorption spectrometer of claim 1, wherein the photoreceiver in combination with the optical switch provide an extinction-ratio from 20 decibels (dB) to 100 dB.

* * * * *